United States Patent
Shwartz et al.

(10) Patent No.: US 11,957,097 B2
(45) Date of Patent: *Apr. 16, 2024

(54) METHODS OF INHIBITING GROWTH OF WEEDS

(71) Applicant: Weedout Ltd., Nes Ziona (IL)

(72) Inventors: Ido Shwartz, Kiryat Ono (IL); Orly Noivirt-Brik, Givataim (IL); Efrat Lidor-Nili, Nes Ziona (IL); Herve Huet, Yehud (IL); Miriam Aminia, Kibbutz Nirim (IL)

(73) Assignee: Weedout Ltd., Nes Ziona (IL)

( * ) Notice: Subject to any disclaimer, the term of this patent is extended or adjusted under 35 U.S.C. 154(b) by 57 days.

This patent is subject to a terminal disclaimer.

(21) Appl. No.: 17/287,574

(22) PCT Filed: Oct. 25, 2019

(86) PCT No.: PCT/IB2019/059171
§ 371 (c)(1),
(2) Date: Apr. 22, 2021

(87) PCT Pub. No.: WO2020/084586
PCT Pub. Date: Apr. 30, 2020

(65) Prior Publication Data
US 2021/0315176 A1    Oct. 14, 2021

Related U.S. Application Data

(60) Provisional application No. 62/750,284, filed on Oct. 25, 2018.

(51) Int. Cl.
*A01H 1/06* (2006.01)

(52) U.S. Cl.
CPC ...................... *A01H 1/06* (2013.01)

(58) Field of Classification Search
None
See application file for complete search history.

(56) References Cited

U.S. PATENT DOCUMENTS

| | | | |
|---|---|---|---|
| 8,437,498 | B2 | 5/2013 | Malsam |
| 11,369,116 | B2 * | 6/2022 | Lidor-Nili .......... C12N 15/8287 |
| 2006/0053686 | A1 | 3/2006 | Halwas |
| 2017/0042102 | A1 | 2/2017 | Safreno |
| 2017/0359943 | A1 | 12/2017 | Calleija et al. |
| 2018/0065749 | A1 | 3/2018 | Cantrell |
| 2019/0208790 | A1 | 7/2019 | Lidor-Nili et al. |
| 2020/0275617 | A1 | 9/2020 | Fabijanski et al. |
| 2020/0281139 | A1 | 9/2020 | Noivirt-Brik et al. |
| 2020/0288656 | A1 | 9/2020 | Lidor-Nili et al. |
| 2020/0288657 | A1 | 9/2020 | Novirt-Brik et al. |
| 2021/0068335 | A1 | 3/2021 | Noivirt-Brik et al. |
| 2021/0127610 | A1 | 5/2021 | Lidor-Nili et al. |
| 2022/0279798 | A1 | 9/2022 | Lidor-Nili |

FOREIGN PATENT DOCUMENTS

| | | |
|---|---|---|
| CN | 1395823 | 2/2003 |
| CN | 101536671 | 9/2009 |
| CN | 102106253 | 6/2011 |
| CN | 103782902 | 5/2014 |
| FR | 2933842 | 1/2010 |
| WO | WO 2014/085774 | 6/2014 |
| WO | WO 2015/164805 | 10/2015 |
| WO | WO 2016/191825 | 12/2016 |
| WO | WO 2017/194399 | 11/2017 |
| WO | WO 2017/203519 | 11/2017 |
| WO | WO 2007/093444 | 7/2018 |
| WO | WO 2019/106666 | 6/2019 |
| WO | WO 2019/106667 | 6/2019 |
| WO | WO 2019/106668 | 6/2019 |
| WO | WO 2019/215581 | 11/2019 |
| WO | WO 2019/215582 | 11/2019 |
| WO | WO 2020/084586 | 4/2020 |
| WO | WO 2020/084586 A9 | 10/2020 |

OTHER PUBLICATIONS

Marcelis et al., 2004, Flower and fruit abortion in sweet pepper in relation to source and sink strength. Journal of experimental Botany, 55(406), 2261-2268. (Year: 2004).*
Yang et al., 2004, Molecular genetic analysis of pollen irradiation mutagenesis in *Arabidopsis*. New phytologist, 164(2), 279-288. (Year: 2004).*
Ribeiro et al., 2014, Involvement of facultative apomixis in inheritance of EPSPS gene amplification in glyphosate-resistant Amaranthus palmeri. Planta, 239, 199-212. (Year: 2014).*
Spaunhorst et al., 2018, Phenology of five Palmer amaranth (*Amaranthus palmeri*) populations grown in northern Indiana and Arkansas. Weed Science, 66(4), 457-469. (Year: 2018).*
Muthoni et al., 2012, Reproductive biology and early generation's selection in conventional potato breeding. Australian Journal of Crop Science, 6(3), 488-497. (Year: 2012).*
Official Action dated Sep. 9, 2022 from US Patent and Trademark Office Re. U.S. Appl. No. 17/052,834. (65 pages).
Final Official Action dated Jun. 30, 2022 from US Patent and Trademark Office Re. U.S. Appl. No. 16/885,311. (30 pages).
Notification of Office Action dated Jun. 24, 2022 From the State Intellectual Property Office of the People's Republic of China Re. Application No. 201780037868.0 and Its Translation Into English. (10 Pages).
English Translation of Notification of Office Action dated Jan. 25, 2022 From the State Intellectual Property Office of the People's Republic of China Re. Application No. 201780037868.0. (5 Pages).
Notice of Allowance dated Feb. 9, 2022 from US Patent and Trademark Office Re. U.S. Appl. No. 16/304,145. (7 pages).
Restriction Official Action dated Aug. 2, 2021 from the US Patent and Trademark Office Re. U.S. Appl. No. 16/885,311. (8 pages).
Official Action dated Feb. 9, 2023 from US Patent and Trademark Office Re. U.S. Appl. No. 17/052,834. (25 pages).

(Continued)

*Primary Examiner* — Cathy Kingdon Worley
*Assistant Examiner* — Santosh Sharma

(57) ABSTRACT

A method of inhibiting growth of a plurality of plants of a weed species of interest in a growth area is provided. The method comprising, artificially pollinating inflorescences of said plants with pollen that reduces fitness of said plants, said artificially pollinating is performed under pollination conditions that inhibit growth of the plants.

18 Claims, No Drawings

(56) References Cited

OTHER PUBLICATIONS

Andreichenko et al. "Possibility of Regulating Seed Formation During Pollination with Mixed Pollen Containing γ-irradiated Pollen", A. A. Bogomolets Kiev Medical Institute, Kiev, Doklady, Biological Sciences, 315(1-6): 699-702, ref. 15, Dec. 1990.
Feng et al. "Effect of Enhanced Ultraviolet-B Radiation on Pollen Germination and Tube Growth of 19 Taxa in Vitro", Environmental and Experimental Botany, 43(1):45-53, Feb. 2000.
Hansen "Precision Pollination. Mechanical Pollination Could end Use of Chemicals or Hand Labor for Thinning." Retrieved from The Internet: www.goodfruit.com, 4 pages, Mar. 18, 2015.
Clarifications Prior to Substantive Examination dated Nov. 18, 2021 From the Instituto Nacional De La Propiedad Industrial Administracion Nacional De Patentes Argentina Re. Applicatiion No. P20170101373 together with English Summary. (6 Pages).
Communication Pursuant to Article 94(3) EPC dated Nov. 20, 2020 From the European Patent Office Re. Application No. 17802323.0. (5 Pages).
International Preliminary Report on Patentability dated Dec. 6, 2018 From the International Bureau of WIPO Re. Application No. PCT/IL2017/050568. (8 Pages).
International Preliminary Report on Patentability dated May 6, 2021 From the International Bureau of WIPO Re. Application No. PCT/IB2019/059171. (7 Pages).
International Preliminary Report on Patentability dated Jun. 11, 2020 From the International Bureau of WIPO Re. Application No. PCT/IL2018/051301. (8 Pages).
International Preliminary Report on Patentability dated Jun. 11, 2020 From the International Bureau of WIPO Re. Application No. PCT/IL2018/051302. (7 Pages).
International Preliminary Report on Patentability dated Jun. 11, 2020 From the International Bureau of WIPO Re. Application No. PCT/IL2018/051303. (8 Pages).
International Preliminary Report on Patentability dated Nov. 19, 2020 From the International Bureau of WIPO Re. Application No. PCT/IB2019/053688. (7 Pages).
International Search Report and the Written Opinion dated Dec. 12, 2019 From the International Searching Authority Re. Application No. PCT/IB2019/059171. (9 Pages).
International Search Report and the Written Opinion dated Aug. 14, 2019 From the International Searching Authority Re. Application No. PCT/IB2019/053690. (13 Pages).
International Search Report and the Written Opinion dated Jul. 14, 2019 From the International Searching Authority Re. Application No. PCT/IB2019/053688. (10 Pages).
International Search Report and the Written Opinion dated Feb. 21, 2019 From the International Searching Authority Re. Application No. PCT/IL2018/051301. (11 Pages).
International Search Report and the Written Opinion dated Aug. 23, 2017 From the International Searching Authority Re. Application No. PCT/IL2017/050568. (11 Pages).
International Search Report and the Written Opinion dated Feb. 24, 2019 From the International Searching Authority Re. Application No. PCT/IL2018/051302. (9 Pages).
International Search Report and the Written Opinion dated Feb. 26, 2019 From the International Searching Authority Re. Application No. PCT/IL2018/051303. (11 Pages).
Office Action dated Jul. 9, 2019 From the Israel Patent Office Re. Application No. 263232 and Its Translation Into English. (5 Pages).
Office Action dated Dec. 10, 2020 From the Israel Patent Office Re. Application No. 263232 and Its Translation Into English. (9 Pages).
Official Action dated Feb. 17, 2021 From the US Patent and Trademark Office Re. U.S. Appl. No. 17/053,089. (45 Pages).
Official Action dated Dec. 30, 2020 from the US Patent and Trademark Office Re. U.S. Appl. No. 16/304,145. (37 pages).
Restriction Official Action dated Oct. 1, 2020 from the US Patent and Trademark Office Re. U.S. Appl. No. 16/304,145. (9 pages).

Supplementary European Search Report and the European Search Opinion dated Oct. 25, 2019 From the European Patent Office Re. Application No. 17802323.0. (9 Pages).
Al-Ahmad et al. "Mitigation of Establishment of *Brassica napus* Transgenes in Volunteers Using A Tandem Construct Containing A Selectively Unfit Gene", Plant Biotechnology Journal, XP055444715, 4(1): Jan. 7-21, 2006. Abstract, p. 16, r-h col. 1st Para, p. 17, 1-h col. 4th Para.
Al-Ahmad et al. "Mitigation Using A Tandem Construct Containing A Selectively Unfit Gene Precludes Establishment of *Brassica napus* Transgenes in Hybrids and Backcrosses With Weedy *Brassica rapa*", Plant Biotechnology Journal, XP055444720, 4(1): 23-33, Published Online Aug. 16, 2005. Abstract, Table S2, p. 31, 1-h col. Lines 10-11, 18-23.
Bae et al. "Production of Unbolting Lines Through Gamma-Ray Irradiation Mutagenesis in Genetically Modified Herbicide-Tolerant Zoysia Japonica", Breeding Science, 59(1): 103-105, 2009.
Chin et al. "Pollination With Irradiated Pollen in Rice—*Oryza sativa* L. I. First (M1) Generation", Heredity, 63(2): 163-170, Published Online Oct. 1, 1989.
Culpepper et al. "Glyphosate-Resistant Palmer Amaranth (Amaranthus Palmeri) Confirmed in Georgia", Weed Science, 54(4):620-626, Jul. 1, 2006.
Daher et al. "Optimization of Conditions for Germination of Cold-Stored *Arabidopsis thaliana* Pollen", Plant Cell Reports, 28: 347-357, 2009.
Germana "Use of Irradiated Pollen to Induce Parthenogenesis and Haploid Production in Fruit Crops", Plant Mutation Breeding and Biotechnology, XP009516584, p., 411-415, Published Online Dec. 31, 2012.
Gressel et al. "A Strategy to Provide Long-Term Control of Weedy Rice While Mitigating Herbicide Resistance Transgene Flow, and Its Potential Use for Other Crops With Related Weeds", Pest Management Science, XP055053395, 65(7): 723- 731, Published Online Apr. 14, 2009.
Jordan et al. "Biorational Management Tactics to Select Against Triazine-Resistant Amaranthus Hybridus: A Field Trial", Journal of Applied Ecology, 36(1): 123-132, Feb. 1999.
Keller et al. "Genetic Introgression From Distant Provenances Reduces Fitness in Local Weed Populations", Journal of Applied Ecology, 37(4): 647-659, Aug. 2000.
Kurtar "Influence of Gamma Irradiation on Pollen Viability, Germination Ability, and Fruit and Seed-Set of Pumpkin and Winter Squash", African Journal of Biotechnology, 8(24): 6918-6926, Dec. 15, 2009.
Kwit et al. "Transgene Introgression in Crop Relatives: Molecular Evidence and Mitigation Strategies", Trends in Biotechnology, XP002794936, 29(6): 284-293, Published Online Mar. 8, 2011.
Lagera et al. "Varying Sugars and Sugar Concentrations Influence In Vitro Pollen Germination and Pollen Tube Growth of *Cassia alata* L.", Journal of Young Investigations, 33(1): 42-45, Jun. 2017.
Li et al. "Effects of Sowing Date on Phenotypic Plasticity of Fitness-Related Traits in Two Annual Weeds on the Songnen Plain of China", PLOS ONE, 10(5): e0127795-1-0127795-15, May 29, 2005.
Ma "Why Don't They Genetically Modify Weeds Instead fo Crops? Wouldn't It Make More Sense to Genetically Alter Species of Weeds to Become Interfile After A Few Generations, Thereby Reducing the Need for Herbicides?", Quora.com, 1 P., Apr. 2, 2014.
Munusamy et al. "Female Reproductive System of Amaranthus as the Target for Agrobacterium-Mediated Transformation", Advances in Biscience and Biotechnology, 4(2): 188-192, Published Online Feb. 28, 2013.
Peixe et al. "Gamma-Irradiated Pollen Induces the Formation of 2n Endosperm and Abnormal Embryo Development in European Plum (*Prunus domestica* L., Cv. 'Rainha Claudia Verde')", Scientia Horticulturae, 86(4): 267-278, Dec. 2000.
Preston ct al. "A Decade of Glyphosate-Resistant Lolium around the World: Mechanisms, Genes, Fitness, and Agronomic Management", Weed Science, 57(4):435-441, Jul. 1, 2009.
Shu "Use of Irradiated Pollen to Induce Pathogenesis and Haploid Production in Fruit Crops", Plant Mutation Breeding and Biotechnology, C30: 412-416, Dec. 2012.

(56) References Cited

OTHER PUBLICATIONS

Tacconi et al. "Kiwifruit Pollination: the Interaction Between Pollen Quality, Pollination Systems and Flowering Stage", Journal of Berry Research, 6(4): 417- 426, Dec. 12, 2016.
Yang et al. "Molecular Genetic Analysis of Pollen Irradiation Mutagenesis in *Arabidopsis*", New Phytologist, XP055615348, 164(2): 279-288, Published Online Sep. 10, 2004.
Relatório de Busca e Parecer [Search Report and Written Opinion] dated Sep. 19, 2022 From the Serviço Público Federal, Ministério da Economia, Instituto Nacional da Propriedade Industrial do Brasil Re. Application No. BR112018074045-4 and Its Summary of Written Opinion in English. (6 Pages).
Yang et al. "Molecular Genetic analysis of Pollen Irradiation Mutagenesis in *Arabidopsis*", New Phytologist, 164(2): 279-288, Sep. 10, 2004.
Final Official Action dated Jun. 22, 2022 from US Patent and Trademark Office Re. U.S. Appl. No. 16/884,362. (32 pages).
Examination Report Under Sections 12 & 13 of the Patents Act, 1970 and the Patents Rules, 2003 dated Jul. 16, 2021 From the Government of India, Intellectual Property India, Patents, Designs, Trade Marks, Geographical Indications, The Patent Office Re. Application No. 201827046713. (7 Pages).
Final Official Action dated Jul. 21, 2021 from the US Patent and Trademark Office Re. U.S. Appl. No. 17/053,089. (34 pages).
Restriction Official Action dated Jul. 12, 2021 from the US Patent and Trademark Office Re. U.S. Appl. No. 16/884,362. (8 pages).
Advisory Action dated Mar. 1, 2022 From the US Patent and Trademark Office Re. U.S. Appl. No. 16/884,097. (11 Pages).
Murphy "The Role of Pollen Allelopathy in Weed Ecology", Weed Technology, 15(4):867-872, Dec. 2001.
Examination Report dated Jan. 27, 2023 From the Australian Government, IP Australia Re. Application No. 2017271409. (5 Pages).
Notification of Office Action and Search Report dated Mar. 10, 2022 From the State Intellectual Property Office of the People's Republic of China Re. Application No. 201880086827.5. (25).
Notification of Office Action dated Jul. 2, 2021 From the State Intellectual Property Office of the People's Republic of China Re. Application No. 201780037868.0 and Its English Summary. (6 Pages).
Translation dated Jul. 14, 2021 of Notification of Office Action dated Jul. 2, 2021 From the State Intellectual Property Office of the People's Republic of China Re. Application No. 200880024068. (6 Pages).
Translation dated Jul. 14, 2021 of Notification of Office Action dated Jul. 2, 2021 From the State Intellectual Property Office of the People's Republic of China Re. Application No. 201780037868.0. (6 Pages).
He "Garden Plant Breeding", China Forestry Publishing House: 174-189, Aug. 1992. Chinese Document only).
English Translation dated Apr. 6, 2022 of Notification of Office Action and Search Report dated Mar. 10, 2022 From the State Intellectual Property Office of the People's Republic of China Re. Application No. 201880086827.5. (4 Pages).
Office Action dated Mar. 31, 2022 From the Israel Patent Office Re. Application No. 263232 and Its Translation Into English. (6 Pages).
Restriction Official Action dated May 3, 2022 from US Patent and Trademark Office Re. U.S. Appl. No. 17/052,834. (6 pages).
Final Official Action dated Sep. 16, 2021 from the US Patent and Trademark Office Re. U.S. Appl. No. 16/304,145. (32 pages).
Interview Summary dated Dec. 13, 2021 from US Patent and Trademark Office Re. U.S. Appl. No. 16/304,145. (2 pages).
Notification of Office Action dated Jan. 9, 2023 From the State Intellectual Property Office of the People's Republic of China Re. Application No. 201780037868.0. (4 Pages).

Notification of Office Action dated Dec. 28, 2022 From the China National Intellectual Property Administration Re. Application No. 201880086827.5. (5 Pages).
Translation dated Jan. 13, 2023 of Notification of Office Action dated Dec. 28, 2022 From the China National Property Administration Re. Application No. 201880086827.5. (3 Pages).
Translation dated Jan. 19, 2023 of Notification of Office Action dated Jan. 9, 2023 From the State Intellectual Property Office of the People's Republic of China Re. Application No. 201780037868.0. (6 Pages).
Office Action dated Feb. 28, 2023 From the Israel Patent Office Re. Application No. 274978. (3 Pages).
Notice of Allowance dated Dec. 21, 2021 from US Patent and Trademark Office Re. U.S. Appl. No. 17/053,089. (12 pages).
Supplementary European Search Report and the European Search Opinion dated Aug. 13, 2021 From the European Patent Office Re. Application No. 18883157.2, ( 120 pages).
Supplementary European Search Report and the European Search Opinion dated Aug. 13, 2021 From the European Patent Office Re. Application No. 18883823.9. (8 Pages).
Official Action dated Nov. 18, 2021 from the US Patent and Trademark Office Re. U.S. Appl. No. 16/884,362 (56 pages).
Official Action dated Nov. 18, 2021 from the US Patent and Trademark Office Re. U.S. Appl. No. 16/885,311. (55 pages).
Kosmrlj et al. "Haploid Induction in Hull-less Seed Pumpkin through Parthenogenesis Induced by X-ray-irradiated Pollen", J. Amu. Soc Hot Sci, vol. 38(4) pp. 310-316,2013.
Kosmrlj ct al. "Haploid Induction in Hull-less Seed Pumpkin through Parthenogenesis Induced by X-ray-irradiated Pollen". Journal of the American Society for Horticultural Science. 138(4):310-316.(Year:2013).
Communication Pursuant to Article 94(3) EPC dated Aug. 12, 2021 From the European Patent Office Re. Application No. 17802323.0. (7 Pages).
Notification of Office Action dated Jan. 25, 2022 From the State Intellectual Property Office of the People's Republic of China Re. Application No. 201780037868.0 with an English Summry. (6 Pages).
Final Official Action dated Nov. 3, 2021 from the US Patent and Trademark Office Re. U.S. Appl. No. 16/884,097. (36 pages).
Communication Pursuant to Article 94(3) EPC dated Dec. 2, 2022 From the European Patent Office Re. Application No. 17802323.0 with Claims. (7 Pages).
Hearing Notice dated Jul. 3, 2023 From the Government of India, Intellectual Property India, The Patent Office Re. Application No. 201827046713. (2 Pages).
Decision on Rejection dated May 29, 2023 From the State Intellectual Property Office of the People's Republic of China Re. Application No. 201880086827.5. (4 Pages).
Official Action dated May 23, 2023 from the US Patent and Trademark Office Re. U.S. Appl. No. 16/884,362. (20 pages).
Brewbaker et al. "Pollen Radiobotany", Radiation Botany, 1: 101-154, 1962.
Requisition by the Examiner dated Jun. 9, 2023 From the Innovation, Science and Economic Development Canada, Canadian Intellectual Property Office Re. Application No. 3,024,079. (6 Pages).
Translation dated Jun. 17, 2023 of Decision on Rejection dated May 29, 2023 From the State Intellectual Property Office of the People's Republic of China Re. Application No. 201880086827.5. (3 pages).
Notice of Allowance dated Jul. 6, 2023 from the US Patent and Trademark Office Re. U.S. Appl. No. 17/052,834. (18 pages).
Communication Pursuant to Article 94(3) EPC dated Jul. 20, 2023 From the European Patent Office Re. Application No. 18883157.2 (5 Pages).

\* cited by examiner

METHODS OF INHIBITING GROWTH OF WEEDS

RELATED APPLICATIONS

This application is a National Phase of PCT Patent Application No. PCT/IB2019/059171 having international filing date of Oct. 25, 2019, which claims the benefit of priority under 35 USC § 119(e) of U.S. Provisional Patent Application No. 62/750,284 filed on Oct. 25, 2018. The contents of the above applications are all incorporated by reference as if fully set forth herein in their entirety.

FIELD AND BACKGROUND OF THE INVENTION

The present invention, in some embodiments thereof, relates to methods of inhibiting growth of weeds.

Weeds have been the major biotic cause of crop yield loses since the origins of agriculture. The potential of weed damages is estimated as 34% loss of crop yield, on average, world-wide [Oerke, E-C., 2006]. In the USA alone, the annual cost of crop losses due to weeds is greater than 26 billion USD [Pimentel D et al., 2000]. Furthermore according to the Weed Science Society of America Weeds are estimated to cause more than 40 billion USD in annual global losses [wssa(dot)net/wssa/weed/biological-control/]. Weeds are thus a major threat to food security [Delye et al., 2013].

Herbicides are the most commonly used and effective weed control tools. Due to the intense selection pressure exerted by herbicides, herbicide resistance is constantly growing and as of 2016 there are over 470 weed biotypes currently identified as being herbicide resistant to one or more herbicides by The International Survey of Herbicide Resistant Weeds (weedscience(dot)org/).

Weeds, like other plants, have several sexual reproduction mechanisms: self-pollination, cross-pollination, or both. Self-pollination describes pollination using pollen from one flower that is transferred to the same or another flower of the same plant. Cross-pollination describes pollination using pollen delivered from a flower of a different plant. Weeds rely on wind, or animals such as bees and other insects to pollinate them.

Since the 1940's the use of sterile organisms has been reported for use in order to reduce pest population and the success of these methods was demonstrated in many cases such as the tsetse fly [Klassen& Curtis, 2005], melon fly [Yosiaki et. al., 2003] and Sweet potato weevil [Kohama et al., 2003].

Planting in the field plants producing sterile pollen for the production of infertile seeds was mentioned but immediately over-ruled due to practical, regulatory and economic reasons. (quora(dot)com/Why-dont-they-genetically-modify-weeds-instead-of-crops).

PCT Publication No. WO2017/203519 discloses a method of weed control comprising artificially pollinating a weed species of interest with pollen of the same species that reduces fitness of the weed species of interest, thereby blocking the next generation of viable weed seeds.

SUMMARY OF THE INVENTION

According to an aspect of some embodiments of the present invention there is provided a method of inhibiting growth of a plurality of plants of a weed species of interest in a growth area, the method comprising, artificially pollinating inflorescences of said plants with pollen that reduces fitness of said plants, said artificially pollinating is performed under pollination conditions that inhibit growth of the plants.

According to some embodiments of the invention, said inhibiting growth is manifested by a reduced biomass as compared to control plants of said weed species of interest not treated with said pollen, being of the same growth conditions and harvesting time from germination.

According to some embodiments of the invention, said biomass is dry weight.

According to some embodiments of the invention, said inhibiting growth is manifested by a reduced number of inflorescences in a life-cycle of the plants as compared to control plants of said weed species of interest not treated with said pollen, being of the same growth conditions and harvesting time from germination.

According to some embodiments of the invention, said inhibiting growth is manifested by a reduced number of spikes in a life-cycle of the plants as compared to control plants of said weed species of interest not treated with said pollen, being of the same growth conditions and harvesting time from germination.

According to some embodiments of the invention, said inhibiting growth is manifested by a reduced number of secondary spikes in a life-cycle of the plants as compared to control plants of said weed species of interest not treated with said pollen, being of the same growth conditions and harvesting time from germination.

According to some embodiments of the invention, said inhibiting growth is manifested by a reduced number of spikelets per inflorescence in a life-cycle of the plants as compared to control plants of said weed species of interest not treated with said pollen, being of the same growth conditions and harvesting time from germination.

According to some embodiments of the invention, said inhibiting growth is manifested by a reduced number of flowers per spikelets in a life-cycle of the plants as compared to control plants of said weed species of interest not treated with said pollen, being of the same growth conditions and harvesting time from germination.

According to some embodiments of the invention, said inhibiting growth is manifested by a reduced number of flowers in a life-cycle of the plants as compared to control plants of said weed species of interest not treated with said pollen, being of the same growth conditions and harvesting time from germination.

According to some embodiments of the invention, said inhibiting growth is manifested by a reduced fraction of leaf axils that developed flowers in a life-cycle of the plants as compared to control plants of the weed species of interest (not treated with the pollen, being of the same growth conditions and harvesting time from germination.

According to some embodiments of the invention, said pollination conditions comprise a single pollination or multiple pollinations.

According to some embodiments of the invention, said multiple pollinations are effected at intervals and wherein at least one interval of said intervals is of 3-30 days.

According to some embodiments of the invention, said multiple pollinations are effected at intervals and wherein at least one interval of said intervals is of 3-21 days.

According to some embodiments of the invention, said multiple pollinations are effected at intervals and wherein at least one interval of said intervals is of 10-60 days.

According to some embodiments of the invention, said multiple pollinations are effected at intervals and wherein at least one interval of said intervals is of 10-45 days.

According to some embodiments of the invention, said multiple pollinations are effected at intervals and wherein at least one interval of said intervals is of 7-30 days.

According to some embodiments of the invention, said multiple pollinations are effected at intervals and wherein at least one interval of said intervals is of 7-21 days.

According to some embodiments of the invention, said multiple pollinations are effected at intervals and wherein at least one interval of said intervals is of 7-14 days.

According to some embodiments of the invention, said multiple pollinations are effected at intervals and wherein at least one interval of said intervals is of at least 14 days.

According to some embodiments of the invention, said inhibition of growth is by at least 20% as compared to control plants of said weed species of interest not treated with said pollen, being of the same growth conditions and harvesting time from germination.

According to some embodiments of the invention, said inhibition of growth is by at least 40% as compared to control plants of said weed species of interest not treated with said pollen, being of the same growth conditions and harvesting time from germination.

According to some embodiments of the invention, said inhibition of growth is by at least 60% as compared to control plants of said weed species of interest not treated with said pollen, being of the same growth conditions and harvesting time from germination.

According to some embodiments of the invention, said pollen is non-genetically modified pollen.

According to some embodiments of the invention, said non-genetically modified pollen is irradiated pollen.

According to some embodiments of the invention, said non-genetically modified pollen is irradiated pollen with x-ray or gamma ray.

According to some embodiments of the invention, said pollen is genetically modified pollen.

According to some embodiments of the invention, said weed species of interest or said pollen is of the *Amaranthus* genus.

According to some embodiments of the invention, said pollination conditions comprise at least 20% of the plants have started flowering.

According to some embodiments of the invention, said pollination conditions comprise at least 50% of the plants have started flowering.

According to some embodiments of the invention, said plants that have started flowering are female plants.

According to some embodiments of the invention, said pollination conditions comprise at least 20% of the plants comprise 6-12 spikes.

According to some embodiments of the invention, said at least 20% of the plants are female plants.

According to some embodiments of the invention, said pollination conditions comprise pollinating 7-30 days following time at which at least 20% of said plants exhibit stigma receptiveness and have started flowering.

According to some embodiments of the invention, said pollination conditions comprise pollinating 7-21 days following time at which at least 20% of said plants exhibit stigma receptiveness and have started flowering.

According to some embodiments of the invention, said pollination conditions comprise pollinating 7-14 days following time at which at least 20% of said plants exhibit stigma receptiveness and have started flowering.

According to some embodiments of the invention, said pollination conditions comprise pollinating:

(i) when total inflorescence length per plant is 20-400 cm;

(ii) when secondary spikes initiate as manifested by a length of secondary spikes in said first pollination is at least 2 cm;

(iii) when 20-50% of the plants have more than a predetermined number of spikes per plant, each spike being longer than 4 cm;

(iv) when 20-50% of the plants have secondary spikes; and/or (v) when 20-50% of the plants have more than 1 spike per plant longer than 4 cm.

According to some embodiments of the invention, a first pollination of said multiple pollinations is effected when total inflorescence length per plant is 20-400 cm, an n (where n is at least 2) pollination of said multiple pollinations is effected when total inflorescence length is 1.3-5 times longer than said length at n−1 pollination of said multiple pollinations.

According to some embodiments of the invention, a first pollination of said multiple pollinations is effected when secondary spikes initiate as manifested by a length of secondary spikes in said first pollination is at least 2 cm, an n pollination (where n is at least 2) of said multiple pollinations is effected when said secondary spikes are 1.3-5 times longer than in n−1 pollination of said multiple pollinations.

According to some embodiments of the invention, a first pollination of said multiple pollinations is effected when a fraction of the plants have more than a predetermined number of spikes per plant, said fraction being 20-50% of the plants, each spike being longer than 4 cm, an n pollination (where n is at least 2) of said multiple pollinations is effected when at least 1.5 fold of said fraction of the plants have more than said predetermined number of spikes per plant, each spike being longer than 4 cm.

According to some embodiments of the invention, said predetermined number of spikes per plant is at least 6 or at least 12.

According to some embodiments of the invention, a first pollination of said multiple pollinations is effected when a fraction of the plants have secondary spikes, said fraction being 20-50% of the plants, an n pollination (where n is at least 2) of said multiple pollinations is effected when at least 1.5 fold of the fraction of the plants have said secondary spikes, a length of secondary spikes in said first pollination is at least 2 cm.

According to some embodiments of the invention, a first pollination of said multiple pollinations is effected when a fraction of the plants have more than 1 spike per plant longer than 4 cm, said fraction being 20-50% of the plants, an n pollination (where n is at least 2) of said multiple pollinations is effected when at least 1.5 fold of the fraction of the plants have more than 1 spike per plant longer than 4 cm.

According to some embodiments of the invention, said weed species of interest is an herbicide resistant weed.

According to some embodiments of the invention, the method further comprises treating said plants with an herbicide.

According to some embodiments of the invention, said treating is prior to said pollinating.

According to some embodiments of the invention, said pollen is coated with an agent selected from the group consisting of a herbicide, ethanol, hormone, steroid, salicylic acid, pesticide, metal and antibiotics.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to methods of inhibiting growth of weeds.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Weeds are plants that are unwanted in any particular environment. They compete with cultivated plants in an agronomic environment and also serve as hosts for crop diseases and insect pests. The losses caused by weeds in agricultural production environments include decreases in crop yield, reduced crop quality, increased irrigation costs, increased harvesting costs, reduced land value, injury to livestock, and crop damage from insects and diseases harbored by the weeds.

The use of herbicides and other chemicals to control weed has generated environmental concern.

PCT Publication No. WO2017/203519 discloses a platform for weed control. The approach is based on producing weed pollen that when artificially applied to the invasive weed out-competes with native fertilization and causes reduction in fitness of the weed, an effect that is typically manifested at the first generation after fertilization.

Surprisingly, the present inventors have now uncovered that under specific conditions such pollen treatment inhibits the growth of the treated plant itself (zero generation), thus the weed control method acts on the treated plants as well as on the next generation, rendering it very effective.

As is illustrated hereinbelow and in the Examples section which follows, the present inventors have shown that treatment of weed (*A. palmeri*) with the artificially produced pollen, according to some embodiments of the invention (e.g., X-ray irradiated) causes a reduction in the number of spikes per plant, and an overall reduction in the number of new spikes (see Example 1). Example 2 shows a significant reduction in the average number of secondary spikes per plant and Example 3 shows a reduction in the number of spikes as well as in weed biomass either wet or dry. The effect on growth inhibition is typically manifested at repeated treatments including an about a two weeks interval therebetween.

Such results are expected to be relevant to other weeds treated according to the present teachings.

Thus, according to an aspect of the invention there is provided a method of inhibiting growth of a plurality of plants of a weed species of interest in a growth area, the method comprising, artificially pollinating inflorescences of said plants with pollen that reduces fitness of said plants, said artificially pollinating is performed under pollination conditions that inhibit growth of the plants.

As used herein "inhibiting growth" or "growth inhibition" refers to reducing the total number of inflorescences (e.g., spikes or spikelets) or flowers of the plant at a predetermined time point following treatment (e.g., the end of the season) as compared to same in a plant of the same species and developmental stage (e.g., harvesting time from germination) under the same conditions not treated with the pollen, also referred to as "control". The definition can relate to the total number of inflorescences or flowers per plant or per field, the latter referring to the average total number of inflorescences or flowers. For dioecious species the growth inhibition is relevant only to the female weeds.

Alternatively or additionally, growth inhibition can be manifested by inhibition of growth of vegetative parts of the plant, e.g., roots (can be determined by root coverage), stems, leaves and the like, according to the above time points and relatively to a control.

According to some embodiments, the growth inhibition is manifested by a reduced biomass as compared to control plants of the weed species of interest not treated with the pollen, being of the same growth conditions and harvesting time from germination (developmental stage).

As used herein "biomass" or "plant biomass" refers to the amount (e.g., measured in grams of air-dry tissue or wet tissue) of a tissue produced from the plant in a growing season. A decrease in plant biomass can be in the whole plant or in parts thereof such as aboveground parts, vegetative biomass, leaf size or area, leaf thickness, roots and seeds. According to a specific embodiment, the plant part is inflorescence.

In this context the term "inflorescence" as used herein is taken to broadly mean a reproductive structure. The form of the inflorescence may vary depending on the plant species in question, however a person skilled in the art would be well aware of the relevant structure(s) to be measured.

According to a specific embodiment, the inhibition of growth is manifested by a reduction in dry weight.

According to a specific embodiment, the inhibition of growth is manifested by a reduction in wet weight, e.g., such as at harvest.

Methods of determining plant biomass are well known in the art.

As used herein, the terms: "reduction", "inhibition", "decrease" which are interchangeably used refer to at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, decrease in growth of the treated plant as compared to a control plant (as defined above).

According to a specific embodiment, the inhibition of growth is by at least 20% as compared to control plants of said weed species of interest not treated with said pollen, being of the same growth conditions and harvesting time from germination.

According to a specific embodiment, the inhibition of growth is by at least 40% as compared to control plants of said weed species of interest not treated with said pollen, being of the same growth conditions and harvesting time from germination.

According to a specific embodiment, the inhibition of growth is by at least 60% as compared to control plants of said weed species of interest not treated with said pollen, being of the same growth conditions and harvesting time from germination.

According to a specific embodiment, growth inhibition is manifested by a reduced number of inflorescences in a life-cycle of the plants as compared to control plants of the weed species of interest not treated with the pollen, being of the same growth conditions and harvesting time from germination (also referred to as "control").

According to a specific embodiment, growth inhibition is manifested by a reduced number of secondary spikes in a life-cycle of the plants as compared to control plants of the weed species of interest not treated with the pollen, being of the same growth conditions and harvesting time from germination (also referred to as "control").

According to a specific embodiment, growth inhibition is manifested by a reduced number of spikelets per inflorescence in a life-cycle of the plants as compared to control plants of the weed species of interest not treated with the pollen, being of the same growth conditions and harvesting time from germination (also referred to as "control").

According to a specific embodiment, growth inhibition is manifested by a reduced number of flowers per spikelets in a life-cycle of the plants as compared to control plants of the weed species of interest not treated with the pollen, being of the same growth conditions and harvesting time from germination (also referred to as "control").

According to a specific embodiment, growth inhibition is manifested by a reduced number of flowers in a life-cycle of the plants as compared to control plants of the weed species of interest not treated with the pollen, being of the same growth conditions and harvesting time from germination (also referred to as "control").

According to a specific embodiment, growth inhibition is manifested by a reduction in a fraction of leaf axils that developed flowers (fraction of total leaf axils) in a life-cycle of the plants as compared to control plants of the weed species of interest (e.g., *Kochia*) not treated with the pollen, being of the same growth conditions and harvesting time from germination (also referred to as "control").

According to a specific embodiment, growth inhibition is manifested by a reduced number of spikes in a life-cycle of the plants as compared to control plants of the weed species of interest not treated with the pollen, being of the same growth conditions and harvesting time from germination.

According to some embodiments of the invention, the effect on growth inhibition can be measured by percent reduction in any, part or all the above parameters.

As used herein "plurality of plants" typically refer to plants is a growth area, as further exemplified hereinbelow.

As used herein the term "weed species of interest" refers to a wild plant growing where it is not wanted and that may be in competition with cultivated plants of interest (i.e., crop-desirable plants). Weeds are typically characterized by rapid growth and/or ease of germination, and/or competition with crops for space, light, water and nutrients. According to some embodiments of the invention, the weed species of interest is traditionally non-cultivated.

According to another embodiment of the invention, the weed is a perennial weed.

According to another embodiment of the invention the weed is a biennial weed.

According to another embodiment of the invention the weed is an annual weed.

According to another embodiment of the invention the weed is a therophyte.

According to an embodiment, the weed is a parasitic plant.

Examples of weed species which can be targeted (mitigated) according to the present teachings include, but are not limited to,

*Amaranthus* species—*A. albus, A. blitoides, A. hybridus, A. palmeri, A. powellii, A. retroflexus, A. rudis, A. spinosus, A. tuberculatus, A. thunbergii, A. graecizans* and *A. viridis; Ambrosia* species—*A. trifida, A. artemisifolia; Lolium* species—*L. multiflorum, L. rigidium, L perenne; Digitaria* species—*D. insularis, D. sanguinalis; Euphorbia* species—*E. heterophylla; Kochia* species—*K. scoparia; Sorghum* species—*S. halepense; Conyza* species—*C. bonariensis, C. canadensis, C. sumatrensis; Chloris* species—*C. truncate; Echinochola* species—*E. colona, E. crus-galli; Eleusine* species—*E. indica; Poa* species—*P. annua; Plantago* species—*P. lanceolata; Avena* species—*A. fatua; Chenopodium* species—*C. album; Setaria* species—*S. viridis, Abutilon theophrasti, Ipomoea* species, *Sesbania*, species, *Xanthium strumarium, Cassia* species, *Sida* species, *Brachiaria* species, *Sporobolus* species—*S. pyramidalis, S. natalensis, S. jacquemontii, S. fertilis, S. africanus S. indicus, Solanum nigrum, Solanum carolinense,* and *Solanum elaeagnifolium.*

Additional weedy plant species found in cultivated areas include *Alopecurus myosuroides, Avena sterilis, Avena sterilis ludoviciana, Brachiaria plantaginea, Bromus diandrus, Bromus rigidus, Cynosurus echinatus, Digitaria ciliaris, Digitaria ischaemum, Digitaria sanguinalis, Echinochloa oryzicola, Echinochloa phyllopogon, Eriochloa punctata, Hordeum glaucum, Hordeum leporinum, Ischaemum rugosum, Leptochloa chinensis, Lolium persicum, Phalaris minor, Phalaris paradoxa, Rottboellia exalta, Setaria faberi, Setaria viridisvar, robusta-alba schreiber, Setaria viridisvar, robusta-purpurea, Snowdenia polystachea, Sorghum Sudanese, Alisma plantago-aquatica, Amaranthus lividus, Ammaniaauriculata, Ammania coccinea, Anthemis cotula, Apera spica-venti, Bacopa rotundifolia, Bidens pilosa, Bidens subalternans, Brassica tournefortii, Bromus tectorum, Camelina microcarpa, Chrysanthemum coronarium, Cuscuta campestris, Cyperus dijformis, Damasonium minus, Descurainia sophia, Diplotaxis tenuifolia, Echium plantagineum, Elatine triandravar, pedicellata, Euphorbia heterophylla, Fallopia convolvulus, Fimbristylis miliacea, Galeopsis tetrahit, Galium spurium, Helianthus annuus, Iva xanthifolia, Ixophorusunisetus, Ipomoea indica, Ipomoea purpurea, Ipomoea sepiaria, Ipomoea aquatic, Ipomoea triloba, Lactuca serriola, Limnocharis flava, Limnophila erecta, Limnophila sessiliflora, Lindernia dubia, Lindernia dubiavar, major, Lindernia micrantha, Lindernia procumbens, Mesembryanthemum crystallinum, Monochoria korsakowii, Monochoria vaginalis, Neslia paniculata, Papaver rhoeas, Parthenium hysterophorus, Pentzia suj fruticosa, Phalaris minor, Raphanus raphanistrum, Raphanus sativus, Rapistrum rugosum, Rotalaindicavar, uliginosa, Sagittaria guyanensis, Sagittaria montevidensis, Sagittaria pygmaea, Salsola iberica, Scirpus juncoidesvar, ohwianus, Scirpus mucronatus, Setaria lutescens, Sida spinosa, Sinapis arvensis, Sisymbrium orientale, Sisymbrium thellungii, Solanum ptycanthum, Sonchus asper, Sonchus oleraceus, Sorghum bicolor, Stellaria media, Thlaspi arvense, Xanthium strumarium, Arctotheca calendula, Conyza sumatrensis, Crassocephalum crepidiodes, Cuphea carthagenenis, Epilobium adenocaulon, Erigeron philadelphicus, Landoltia punctata, Lepidium virginicum, Monochoria korsakowii, Solanum americanum, Solanum nigrum, Vulpia bromoides, Youngia japonica, Hydrilla verticillata, Carduus nutans, Carduus pycnocephalus, Centaurea solstitialis, Cirsium arvense, Commelina diffusa, Convolvulus arvensis, Daucuscarota, Digitaria ischaemum, Echinochloa crus-pavonis, Fimbristylis miliacea, Galeopsis tetrahit, Galium spurium, Limnophila erecta, Matricaria perforate, Papaver rhoeas,*

*Ranunculus acris, Soliva sessilis, Sphenoclea zeylanica, Stellaria media, Nassella trichotoma, Stipa neesiana, Agrostis stolonifera, Polygonum aviculare, Alopecurus japonicus, Beckmannia syzigachne, Bromus tectorum, Chloris inflate, Echinochloa erecta, Portulaca oleracea,* and *Senecio vulgaris.*

According to a specific embodiment the weed species is selected from or belong to the group consisting of *Amaranthus: A. palmeri, A. tuberculatus, Lolium rigidum, Lolium multiflorum, Lolium perenne Ambrosia: A. trifida, A. artemisiifolia, Kochia scoparia, Conyza: C. canadensis, C. bonariensis, Echinochloa, Alopecurus myosuroides, Sorghum halepense, Digitaria insularis, Eleusine indica, Avena fatua, Euphorbia Heterophylla* and *Chenopodium album.*

According to an embodiment, the weed is a parasitic plant. Examples of parasitic plants include, but are not limited to, *Striga* sp, *Orobanche* sp, *Cuscuta* sp, Mistletoe.

According to a specific embodiment, the weed species is not of the *Amaranthus* genus e.g., *A. palmeri.*

Different weed may have different growth habits and therefore specific weeds usually characterize a certain crop in given growth conditions.

According to a specific embodiment, the weed is an herbicide resistant weed.

According to a specific embodiment, weed is defined as herbicide resistant when it meets the Weed Science Society of America (WSSA) definition of resistance.

Accordingly, WSSA defines herbicide resistance as "the inherited ability of a plant to survive and reproduce following exposure to a dose of herbicide normally lethal to the wild type. Alternatively, herbicide resistance is defined as "The evolved capacity of a previously herbicide-susceptible weed population to withstand an herbicide and complete its life cycle when the herbicide is used at its normal rate in an agricultural situation" (Source: Heap and Lebaron. 2001 in Herbicide Resistance and World Grains).

As used herein the phrase "weed control" refers to suppressing growth and optionally spread of a population of at least one weed species of interest and even reducing the size of the population in a given growth area.

According to a specific embodiment, the growth area is an urban area, e.g., golf courses, athletic fields, parks, cemeteries, roadsides, home gardens/lawns and the like.

According to an additional or alternative embodiment, the growth area is a rural area.

According to an additional or an alternative embodiment, the growth area is an agricultural growth area e.g., open field, greenhouse, plantation, vineyard, orchard and the like.

According to a specific embodiment, the growth area comprises crop plants (e.g., from seeds to full grown plants and anywhere in-between).

As mentioned, weed control according to the present teachings is effected by reducing fitness of the at least one weed species of interest.

As used herein "fitness" refers to the relative ability of the weed species of interest to develop, reproduce or propagate and transmit its genes to the next generation. As used herein "relative" means in comparison to a weed of the same species not having been artificially pollinated with the pollen of the invention and grown under the same conditions.

It will be appreciated that the effect of pollen treatment according to the present teachings is already manifested prior to first generation after fertilization i.e., on the treated plant itself.

The fitness may be affected by reduction in productiveness, propagation, fertility, fecundity, biomass, biotic stress tolerance, abiotic stress tolerance and/or herbicide resistance.

As used herein "productivity" refers to the potential rate of incorporation or generation of energy or organic matter by an individual, population or trophic unit per unit time per unit area or volume; rate of carbon fixation.

As used herein "fecundity" refers to the potential reproductive capacity of an organism or population, measured by the number of gametes.

According to a specific embodiment, the pollen affects any stage of seed development or germination.

According to a specific embodiment, the reduction in productiveness is manifested by at least one of:
 (i) inability to develop an embryo;
 (ii) embryo abortion;
 (iii) seed non-viability;
 (iv) seed that cannot fully develop; and/or
 (v) seed that is unable to germinate.

It will be appreciated that when pollen reduces the productiveness, fertility, propagation ability or fecundity of the weed in the next generation it may be referred to by the skilled artisan as sterile pollen, though it fertilizes the weed of interest. Hence, sterile pollen as used herein is still able to fertilize but typically leads to seed developmental arrest or seed abortion.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization and optionally second generation after fertilization and optionally third generation after fertilization.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization.

According to a specific embodiment, reduced fitness results from reduction in tolerance to biotic or abiotic conditions e.g., herbicide resistance.

Non-limiting examples of abiotic stress conditions include, salinity, osmotic stress, drought, water deprivation, excess of water (e.g., flood, waterlogging), etiolation, low temperature (e.g., cold stress), high temperature, heavy metal toxicity, anaerobiosis, nutrient deficiency (e.g., nitrogen deficiency or nitrogen limitation), nutrient excess, atmospheric pollution, herbicide, pesticide and UV irradiation.

Biotic stress is stress that occurs as a result of damage done to plants by other living organisms, such as bacteria, viruses, fungi, parasites, beneficial and harmful insects, weeds, and cultivated or native plants.

Examples of herbicides which are contemplated according to the present teachings, include, but are not limited to, ACCase inhibitors, ALS inhibitors, Photosystem II inhibitors, PSII inhibitor (Ureas and amides), PSII inhibitors (Nitriles), PSI Electron Diverter, PPO inhibitors, Carotenoid biosynthesis inhibitors, HPPD inhibitors, Carotenoid biosynthesis (unknown target), EPSP synthase inhibitors, Glutamine synthase inhibitors, DHP synthase inhibitors, Microtubule inhibitors, Mitosis inhibitors, Long chain fatty acid inhibitors, Cellulose inhibitors, Uncouplers, Lipid Inhibitors (thiocarbamates), Synthetic Auxins, Auxin transport inhibitors, Cell elongation inhibitors, Antimicrotubule mitotic disrupter, Nucleic acid inhibitors or any other form of herbicide site of action.

As used herein "development of flowers" refers to any stage of flowering i.e., from development of non-vegetative organs till anthesis or to fully receptive stigma. Flowers can be unisexual (with either male or female organs) or bisexual (with male stamens and female pistils). Flowering plant species can have separate male and female flowers on the same plant (monoecious) or separate male and female individuals within the population (dioecious).

Specifically, prior to flowering, flower organs are developed to become ready for reproduction. Pre-flowering stages are based on the development of non-vegetative i.e., sexual organs (male part and female part).

The Pre-Flowering stage includes:
1. Pollen Formation—In anther, pollens are formed and developed.
2. Ovary Development—The ovary, the chamber that envelops the ovule, is formed. The tissues in ovule are formed and start developing.
3. Formation of Embryo Sac. The embryo sac, the storage of nutrients for the baby (embryo) to grow until it reaches out of soil and gets own nutrients by photosynthesis, is formed. When the embryo sac is completely developed, the other flower organs are also ready for flowering and fertilization.

Typically a flower is ready for fertilization 1 day prior to flowering. Within the day between pre-flowering and flowering stages, a flower begins pollination.

Once pollen in the anther (male reproductive part) and the embryo sac in the ovule (female reproductive part) are fully developed, the next stage is flowering, i.e., anthesis.

Stigmas of *A. tuberculatus* var. *rudis* unfertilized female flowers can persist indefinitely until pollen reaches them, consistent with observations on another dioecious species, *A. cannabinus* (Quinn et al. J. Torrey Bot. Soc. 127: 83-86 2000). After fertilization, the stigmas dry out. (Costea et al., Canadian Journal of Plant Science, 2005, 85(2): 507-522).

Anthesis is the period during which a flower is fully open and functional. It may also refer to the onset of that period.

According to a specific embodiment, said determining development of flowers comprises determining pre-flowering.

According to a specific embodiment, said determining development of flowers comprises determining development of inflorescence meristem.

According to a specific embodiment, said determining development of flowers comprises determining anthesis.

According to a specific embodiment, said determining development of flowers comprises identification of female structures.

According to a specific embodiment, said determining development of flowers comprises identification of male structures.

According to a specific embodiment, determining flowering is performed once per plant per (weed or crop) growth season.

According to a specific embodiment, determining flowering is performed multiple times per plant or growth area per (weed or crop) growth season. In this case determining is also referred to as "monitoring".

Determining flowering can be effected at the individual level or according to a population level at various regions.

Methods of determining pollination are known in the art.

Conventional methods for determining flowering include dissecting plants under magnification to determine the presence of either a vegetative or reproductive structure at the meristem.

A less time-consuming method often used by plant breeders to determine the flowering is to monitor emergence of the inflorescence, otherwise known as "emergence" or "heading time". Heading time is defined as the moment when the first inflorescence is exerted from the leaf sheaths and becomes visible to the naked eye.

A further method for determining the start of flowering is to monitor anthesis, which is the moment pollen is released from the anthers A widely used method for determining the start of flowering in the field involves repeated visual inspection of plots to estimate the number of flowering plants present in a plot. It is conventionally accepted in agronomics that a plot is "flowering" when 50% of plants in a plot exhibit emerged inflorescences. This technique will give a rough idea as to whether a group of plants is flowering.

US Patent Publication No. 20090226042 teaches a method of determining the point at which a plant starts to flower. Accordingly, this can be effected by determining the start of flowering on an individual plant basis by measuring the reproductive structures of plants from digital images of these structures and deducing the start of flowering from the measurements and average growth rates. Also provided is an apparatus for determining the start of flowering in plants, particularly in a high-throughput manner.

According to an embodiment of the application determining flowering comprises the steps of digitally imaging an inflorescence of a plant; and measuring the inflorescence from the digital image; calculating the flowering (e.g., start of) from the average growth rate of inflorescences and the measurements derived from the calculation.

Advantageously, the method of this embodiment of the invention allows the start of flowering to be accurately determined on an individual plant level.

Furthermore, this method provides means to discriminate flowering and non-flowering plants from the presence or absence of an inflorescence.

The dimensions (typically the area, but this may also be the length and/or width) of the inflorescence is measured from the digital image and using this information and the average growth rate for inflorescences (of the plant species or variety in question) one may back calculate the point of emergence of the inflorescence.

According to embodiments of the invention and this embodiment in particular determining development of flowers is effected by integrating plant data and/or field data with literature data such as will be apparent infra.

For example, the average growth rate of an inflorescence of a particular plant species or variety is 10 cm per day, and the observed size of an inflorescence of a plant of the same species or variety is 30 cm, therefore it can be deduced that the inflorescence appeared 3 days before the moment of the observation. Therefore the start of flowering would also have been 3 days before the moment of the observation.

According to an embodiment of the invention, to determine flowering requires a detectable and measurable inflorescence to be present at the time of imaging, however this need not be the first inflorescence. Thus contemplated is measuring flowering of first inflorescence, second inflorescence etc. Furthermore, the inflorescence should not have reached its maximum size at the time of imaging. This would require observations of a sufficient frequency so that at least one observation is performed between emergence of the inflorescence and before it reaches its maximum size. The frequency of observations can readily be determined by a person skilled in the art and will of course depend upon the species or variety in question.

Such a method is particularly suited to handling large numbers of plants in a high throughput manner, whilst retaining a high level of accuracy, since flowering can be determined on an individual plant level.

According to a specific embodiment, determining at the level of an individual plant is also advantageous for weed in which flowering is synchronized such as due to environmental reasons. For instance, synchronized flowering is taken place in *Amaranthus palmeri* (*A. palmeri*) weed. Korres and Norsworthy (2017), Weed Science, 65(4):491-503 conducted field experiments in Arkansas University during the summers of 2014 and 2015 and they investigated *A. palmeri* flowering initiation and progress. According to their observations *A. palmeri* weed emerges at late June and its flowering initiation starts at the end of July or the beginning of August (about 30-40 days after emergence) and continues for approximately 40-50 days. In addition, it has been demonstrated that the flowering period of *A. palmeri* population is relatively synchronized and it is independent from the plant emergence date as it is regulated by environmental conditions such as day length and temperature (Keeley et. Al, 1987; Weed Science Vol. 35, No. 2 (March, 1987), pp. 199-204; Korres and Norsworthy (2017), Weed Science, 65(4):491-503; Clay et al., 2016; Weed Science Society of America, Annual Meeting. San Juan, Puerto Rico, Feb. 8-11, 2016). Similar observations regarding flowering synchronization were also reported for *A. tuberculatus* (Wu and Owen, 2014; Weed Science, 62(1):107-117). Hence, integrating field data which determines a pre-flowering stage such as described above is sufficient together with literature data to determine anthesis and pollinating at the relevant stage.

Such methods can be performed using an apparatus for determining flowering, which apparatus typically comprises one or more digital cameras with sufficient resolution for imaging emerging plant inflorescences; and computer means for detecting and measuring plant inflorescences and for deriving the start of flowering from said measurements and average growth rates of inflorescences.

Determining flowering can be effected in situ (e.g., in the field).

In this case, one or more digital cameras are arranged to move over the plants to take images of the plant inflorescences.

According to a specific embodiment, plants are presented to the camera in such a way that individual plants can be discriminated and identified. This allows assessment of population homogeneity for flowering time using existing statistical techniques. Digital cameras suitable for imaging emerging plant inflorescences are typically those allowing the inflorescences imaged to have a minimum size of about 100 pixels.

The computer means for detecting and measuring plant inflorescences comprises image-processing software. Typically, such software uses features specific to inflorescences to distinguish these from, say, vegetative organs (stems and leaves). For example, flowers often exhibit a different color and/or texture than the rest of the plant. Rollin et al., 2016 discusses (Rollin, O., Benelli, G., Benvenuti, S. et al. Agron. Sustain. Dev. (2016) 36: 8.) that flower shape and color play a key role in routing insect foraging flights (Menzel and Shmida 1993). Many Brassicaceae species reflect ultraviolet radiation to attract insect pollinators (Yoshioka et al. 2005). These can be used in a similar way for detection purposes.

For instance, where the range of colors displayed by immature inflorescences is close to that of stems or leaves, the software uses differences in shape and pattern to distinguish from the more granular structure of the inflorescence which results in a higher pixel-to-pixel variation than that of the leaves or stem. Topological cues can also be used to refine detection. For example, inflorescences are usually found at the top of the plant and they are always connected to a stem.

An example of digital images processing of images of weed plants from which the plant inflorescences may be measured. A starting image is subjected to a so-called "thresholding" process involves removal of all non-plant parts. Thresholding is achieved by virtue of the background and non-plant parts exhibiting a different color range to the plant organs. After that an image after thresholding is produced. This is followed by a statistical method termed "color variation analysis" which is applied to the remaining pixels to determine which parts exhibit textural properties akin to that of inflorescences. An image after color variation analysis is prepared. Literature data of inflorescence color and texture would be required for this step, Objects classified as "non-inflorescence" through the process of color variation analysis are removed. Finally, the dimensions of the remaining objects, classified as "inflorescences", are recorded by the software. Since some parts of the inflorescences can be hidden by other plant parts, such as leaves, it is preferable to refine the measurements by averaging the results obtained from several pictures, say at least 3 pictures or images and generally not more than 6.

Statistical analysis may also be carried out on data collected using the unique identifier. For example, statistical data analysis to determine the start of flowering may be based on the following three steps. The first step corrects for the presence of an inflorescence based on logic rules, i.e. assumes that there is consistency between the six pictures or images taken of any one image, that there are no inflorescences on plants that are smaller than a certain size and that inflorescences do not disappear once present. The second step estimates the speed of inflorescence growth in the entire batch of plants. In this step, inflorescence size is corrected for plant size, an exponential inflorescence growth is assumed in the first week of growth and a date for inflorescence emergence is estimated for each plant. In the third step, population means of the inflorescence emergence date and standard errors on these estimates are calculated based on survival method (Cox models).

If, for example, plants are imaged at weekly intervals, the presence of an inflorescence on an image allows the start of flowering to be determined with a resolution of one week. More thorough data analysis making use of inflorescence size may be used to interpolate between two images and to determine the start of flowering with a lower resolution for individual plants More thorough data analysis making use of inflorescence size may also be used to provide more reliable estimates of the mean start of flowering for a population of plants considering the presence of plants that were not flowering at the time of last imaging.

Additional information may be recorded such as species (e.g., based on light reflectance), date, inflorescence measurements and/or other measurements (e.g., height, plants per plot, density, distribution, geographical location, male and/or female organs), and any other quantitative or qualitative observations made on the plant. Data contained in the database can be retrieved by means of appropriate software.

Molecular determination of transition to flowering such as LEAFY and APETALA 1 in *A. thaliana* and their respective homologoues FLORICAULA and SQUAMOSA in *A. majus* (Krizek and Fletcher nature reviews genetics 2005).

Additional information will include identification depending on floral odor and fragrance and relies on volatiles such as described in Schiestl and Marion Poll., 2002.

Therefore, chemical determination of flowering can be used for detection. In Rollin et al., 2016 (Rollin, O., Benelli, G., Benvenuti, S. et al. Agron. Sustain. Dev. (2016) 36: 8.) Olfactory and tactile cues were discussed as insect recognition patterns that can be used also for detection purposes. A mechanism for identification and recognition of flowers also consists in the production and emission of volatile compounds, mainly terpenoids and benzenoids (van Schie et al. 2006). The two dominant components of the fragrance of *Cirsium* species (Asteraceae), benzaldehyde and phenylacetaldehyde, attract several orders of generalist insect pollinators (Theis 2006). Fragrance of their flowers is emitted in dynamic patterns that maximize pollinator attraction (Theis et al. 2007).

Determination of flowering based on pollen in the air in the growth area is also another measure. The skilled in the art would know how to determine air pollen. For instance, Vurkard volumetric spore trap, which vacuums up air through a slit and captures floating grains. Pollen count can also be measured by attaching a rotating rod with a sticky substance. After 24 hours, the amount of pollen that has adhered to the rod is analyzed.

Yet another method is determining vegetative portions which are often indicative of later flowering. For instance by counting the number of leaves, which in some weed species is indicative of flowering.

According to a specific embodiment, pollinating is effected at stigma receptive stage.

According to a specific embodiment, pollinating is effected at anthesis.

According to a specific embodiment, pollinating is effected prior to anthesis but once the stigma is receptive.

According to a specific embodiment, pollinating is effected once per crop (that is present in the field) growth season.

According to a specific embodiment, pollinating is effected a number of times (e.g., 1-150 times) per (weed or crop) growth season.

According to a specific embodiment, pollinating is effected prior to or at anthesis.

Each of the determining flowering and/or pollinating can be effected more than once per plot. For instance, pollination can be effected post crop emergence and prior to crop harvesting. For instance, in the weeds *Amaranthus palmeri* and *Amaranthus tuberculatus* interfering in a corn, soybean or cotton field pollination will be applied during late season. Alternatively or additionally, after crop harvesting in order to avoid seedbank replenishment. Each and any of the above tools can be coupled to an agricultural precision tool.

Precision agriculture (PA), satellite farming or site specific crop management (SSCM) is a farming management concept based on observing, measuring and responding to inter and intra-field variability in crops. The goal of precision agriculture research is to define a decision support system (DSS) for whole farm management with the goal of optimizing returns on inputs while preserving resources Among these many approaches is a phytogeomorphological approach which ties multi-year crop growth stability/characteristics to topological terrain attributes. The interest in the phytogeomorphological approach stems from the fact that the geomorphology component typically dictates the hydrology of the farm field.

The practice of precision agriculture has been enabled by the advent of GPS and GNSS. The farmer's and/or researcher's ability to locate their precise position in a field allows for the creation of maps of the spatial variability of as many variables as can be measured (e.g. crop yield, terrain features/topography, organic matter content, moisture levels, nitrogen levels, pH, EC, Mg, K, and others). Similar data is collected by sensor arrays mounted on GPS-equipped combine harvesters. These arrays consist of real-time sensors that measure everything from chlorophyll levels to plant water status, along with multispectral imagery. This data is used in conjunction with satellite imagery by variable rate technology (VRT) including seeders, sprayers, etc. to optimally distribute resources.

Precision agriculture has also been enabled by unmanned aerial vehicles like the DJI Phantom which are relatively inexpensive and can be operated by novice pilots. These systems, commonly known as drones, can be equipped with hyperspectral or RGB cameras to capture many images of a field that can be processed using photogrammetric methods to create orthophotos and NDVI maps.

According to a specific embodiment, the use of a technique called multispectral analysis is used. This technique looks at how strongly plants absorb or reflect different wavelengths of sunlight, they can discover which weed are flowering and which not.

Sensors attached to moving machinery (ground or aerial) can even take measurements on the run. For example, multispectral sensors mounted on a tractor's spraying booms.

Thus, data can be collected on the go i.e., in real time while treating the crop/weed.

Alternatively, pollinating can be effected based on data deduced from former measurements.

As used herein "pollen" refers to viable pollen that is able to fertilize the weed species of interest and therefore competes with native pollination.

Alternatively, when native pollen competition does not exist, or very low levels of native pollen are present, pollination by the designed pollen inhibits apomixis of weeds and by this reduces their quantities as well [Ribeiro et al. 2012 Abstracts of the Weed Science Society of America Annual Meeting. www(dot)wssaabstracts(dot)com/public/9/abstract-438(dot)html].

According to a specific embodiment, the pollen is of the same species as of the target weed (e.g., invasive, aggressive weed).

According to a specific embodiment, the pollen exhibits susceptibility to a single growth condition e.g., herbicide, temperature.

According to a specific embodiment, the pollen exhibits susceptibility to multiple growth conditions e.g., different herbicides.

According to a specific embodiment, the pollen is non-genetically modified.

The pollen may therefore be of a naturally occurring plant that reduces the fitness of the at least one weed species of interest. According to a specific embodiment, *A. palmeri* or *A. tuberculatus* susceptible seeds are available from the Agriculture Research Service National Plant Germplasm System plant introduction (USDA-ARS_NPGS PI) as well as from various locations in Israel.

Alternatively or additionally, the pollen may be of a plant that has been selected towards producing pollen that reduces the fitness of the at least one weed species of interest.

Selection can be effected by way of exposing the weed to various concentrations of, for example, a herbicide or a plurality of different herbicides, and selecting individuals which show increased susceptibility to the herbicide or different herbicides. Alternatively or additionally, different plants exhibiting susceptibility to different herbicides can be crossed to generate a plant exhibiting susceptibility to a number of herbicides of interest.

It will be appreciated that such breeding need not engage into pedigree breeding programs as the mere product is the pollen of a weedy plant.

According to a specific embodiment, there is provided a method of producing pollen that reduces fitness of at least one weed species of interest, the method comprising treating the weed species of interest (e.g., seeds, seedlings, tissue/cells) or pollen thereof with an agent that reduces fitness.

When needed (such as when treating that weed (e.g., seeds, seedlings, tissue/cells) the method further comprises growing or regenerating the plant so as to produce pollen.

According to a specific embodiment, the method comprises harvesting pollen from the weed species of interest following treating with the agent that reduces the fitness.

It will be appreciated that the pollen may be first harvested and then treated with the agent (e.g., radiation) that reduces the fitness of the weed species of interest.

Alternatively or additionally, the pollen is produced from a plant having an imbalanced chromosome number (genetic load) with the weed species of interest.

Thus, for example, when the weed of interest is diploid, the plant producing the pollen is treated with an agent rendering it polyploid, typically, tetraploids are selected, such that upon fertilization with the diploid female plant an aborted or developmentally arrested, not viable seed set are created. Alternatively, a genomically imbalanced plant is produced which rarely produces a seed set.

According to a specific embodiment, the weed (or a regenerating part thereof or the pollen) is subjected to a polyploidization protocol using a polyploidy inducing agent, that produces plants which are able to cross but result in reduced productiveness.

Thus, according to some embodiments of the invention, the polyploid weed has a higher chromosome number than the wild type weed species (e.g., at least one chromosome set or portions thereof) such as for example two folds greater amount of genetic material (i.e., chromosomes) as compared to the wild type weed. Induction of polyploidy is typically performed by subjecting a weed tissue (e.g., seed) to a G2/M cycle inhibitor.

Typically, the G2/M cycle inhibitor comprises a microtubule polymerization inhibitor.

Examples of microtubule cycle inhibitors include, but are not limited to, oryzalin, colchicine, colcemid, trifluralin, benzimidazole carbamates (e.g. nocodazole, oncodazole, mebendazole, R 17934, MBC), o-isopropyl N-phenyl carbamate, chloroisopropyl N-phenyl carbamate, amiprophosmethyl, taxol, vinblastine, griseofulvin, caffeine, bis-ANS, maytansine, vinbalstine, vinblastine sulphate and podophyllotoxin.

According to a specific embodiment, the microtubule cycle inhibitor is colchicine.

Still alternatively or additionally, the weed may be selected producing pollen that reduces fitness of the weed species of interest by way of subjecting it to a mutagenizing agent and if needed further steps of breeding.

Thus, weed can be exposed to a mutagen or stress followed by selection for the desired phenotype (e.g., pollen sterility, herbicide susceptibility).

Examples of stress conditions which can be used according to some embodiments of the invention include, but are not limited to, X-ray radiation, gamma radiation, particle irradiation such as alpha, beta or other accelerated particle, UV radiation or alkylating agents such as NEU, EMS, NMU and the like. The skilled artisan will know which agent to select.

According to a specific embodiment, the stress is selected from the group consisting of X-ray radiation, gamma radiation, UV radiation. For example. Pollen of the weed can be treated with the agent that reduces the fitness (e.g., radiation) following harvest.

Guidelines for plant mutagenesis are provided in K Lindsey Plant Tissue Culture Manual—Supplement 7: Fundamentals and Applications, 1991, which is hereby incorporated in its entirety.

Other mutagenizing agents include, but are not limited to, alpha radiation, beta radiation, neutron rays, heating, nucleases, free radicals such as but not limited to hydrogen peroxide, cross linking agents, alkylating agents, BOAA, DES, DMS, EI, ENH, MNH, NMH Nitrous acid, bisulfate, base analogs, hydroxyl amine, 2-Naphthylamine or alfatoxins.

According to a specific embodiment, the radiation is X-ray radiation.

According to a specific embodiment, the dose of radiation (X-ray) is 150-300 Gy e.g., 150 or 300 Gy, such as in the case of *Amaranthus* genus (e.g., *A. palmeri*).

Alternatively or additionally, the pollen may be genetically modified pollen (e.g., transgenic pollen, DNA-editing).

Numerous methods are known for exploiting genetic modification to render it suitable for reducing the fitness of a weed species of interest.

Thus, according to a specific embodiment, the pollen is genetically modified pollen.

According to other specific embodiments, the trait being inherited upon artificial pollination with the pollen of the invention is selected from the group consisting of embryo abortion, seed non-viability, seeds with structural defects, seeds that are unable to germinate, abiotic/biotic stress susceptibility (e.g., herbicide susceptibility) or induced death or sensitivity upon chemical or physical induction or any other inherited property that will enable controlled reduction of weed population size.

Often sterile pollen results in a seedless plant. A plant is considered seedless if it is not able to produce seeds, traces of aborted seeds or a much-reduced number of seeds. In other cases the pollen will produce plants with seeds that are unable to germinate or develop e.g., no embryo or embryo abortion.

According to a specific embodiment, the pollen is genetically modified to express an exogenous transgene that upon fertilization will reduce fitness of the weed of interest (next generation). Such a gene is termed a "disrupter gene". According to some embodiments, the disrupter gene causes kills the weed species of interest, accordingly it is termed a "death gene".

According to a further aspect of the invention there is provided a method of producing pollen, the method comprising:

(a) growing weed producing pollen that reduces fitness of at least one weed species of interest; and
(b) harvesting the pollen.

Thus the pollen product producing weed is grown in dedicated settings, e.g., open or closed settings, e.g., a greenhouse. According to a specific embodiment, the growth environment for the manufacture of the pollen does not include crop plants or the weed species of interest. For example, the growth area includes an herbicide susceptible weed variant but not an herbicide resistant weed variant (of the same species). Another example, the growth environment comprises a GM weed with a destructor gene the weed being fertile and producing pollen, but doesn't include the weed in which the destructor gene is expressed.

According to a specific embodiment, growing the weed producing pollen that reduces fitness is effected in a large scale setting (e.g., hundreds to thousands m²).

According to some embodiments of the invention, the weed producing pollen comprises only male plants.

Harvesting pollen is well known in the art. For example, by the use of paper bags.

Another example is taught in U.S. 20060053686, which is hereby incorporated by reference in its entirety.

Once pollen is obtained it can be stored for future use. Examples of storage conditions include, but are not; limited to, storage temperatures in Celsius degrees e.g., −196, −160, −130, −80, −20, −5, 0, 4, 20, 25, 30 or 35; percent of relative humidity e.g., 0, 10, 20, 30, 40, 50, 60, 70, 80, 90 or 100. Control over humidity can be achieved by using a dehydrating agent as known in the art. Additionally, the pollen can be stored in light or dark.

Alternatively, the pollen product of the present teachings is subjected to a post-harvest treatment.

Thus, according to an aspect of the invention there is provided a method of producing pollen for use in artificial pollination, the method comprising:
(a) obtaining pollen that reduces fitness of at least one weed species of interest, e.g., as described herein; and
(b) treating the pollen for use in artificial pollination.

Accordingly, there is provided a composition of matter comprising weed pollen that reduces fitness of at least one weed species of interest, the pollen having been treated for improving its use in artificial pollination.

Examples of such treatments include, but are not limited to coating, priming, formulating, chemical inducers, physical inducers [e.g., potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide], solvent solubilization, drying, heating, cooling and irradiating (e.g., gamma, UV, X-ray, particle).

Additional ingredients and additives can be advantageously added to the pollen composition of the present invention and may further contain sugar, potassium, calcium, boron, and nitrates. These additives may promote pollen tube growth after pollen distribution on flowering plants.

In some embodiments, the pollen composition of the present invention contains dehydrated or partially dehydrated pollen.

Thus, the pollen composition may comprise a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, a herbicide or a pesticide.

Other ingredients and further description of the above ingredients is provided hereinbelow.

Under ordinary conditions of storage and use, the composition of the present invention may contain a preservative to prevent the growth of microorganisms.

The preventions of the action of microorganisms can be brought about by various antibacterial and antifungal agents, for example, parabens, chlorobutanol, sorbic acid, and the like. Antioxidants may also be added to the pollen suspension to preserve the pollen from oxidative damage during storage. Suitable antioxidants include, for example, ascorbic acid, tocopherol, sulfites, metabisulfites such as potassium metabisulfite, butylhydroxytoluene, and butylhydroxyanisole.

Thus, pollen compositions that may also be used but not limited to mixtures with various agricultural chemicals and/or herbicides, insecticides, miticides and fungicides, pesticidal and biopesticidal agents, nematocides, bactericides, acaricides, growth regulators, chemosterilants, semiochemicals, repellents, attractants, pheromones, feeding stimulants or other biologically active compounds all of which can be added to the pollen to form a multi-component composition giving an even broader spectrum of agricultural protection.

Thus in the artificial pollination method of the present invention can be applied together with the following herbicides but not limited to: ALS inhibitor herbicide, auxin-like herbicides, glyphosate, glufosinate, sulfonylureas, imidazolinones, bromoxynil, delapon, dicamba, cyclohezanedione, protoporphyrionogen oxidase inhibitors, 4-hydroxyphenyl-pyruvate-dioxygenase inhibitors herbicides.

In some embodiments, the pollen can be combined with appropriate solvents or surfactants to form a formulation. Formulations enable the uniform distribution of a relatively small amount of the pollen over a comparatively large growth area. In addition to providing the user with a form of a pollen that is easy to handle, formulating can enhance its fertilization activity, improve its ability to be applied to a plant, enable the combination of aqueous-soluble and organic-soluble compounds, improve its shelf-life, and protect it from adverse environmental conditions while in storage or transit.

Numerous formulations are known in the art and include, but are not limited to, solutions, soluble powders, emulsifiable concentrates, wettable powders, liquid flowables, and dry flowables. Formulations vary according to the solubility of the active or additional formulation ingredients in water, oil and organic solvents, and the manner the formulation is applied (i.e., dispersed in a carrier, such as water, or applied as a dry formulation).

Hence, contemplated are wet (e.g., liquid) as well as dry formulations.

Solution formulations are designed for those active ingredients that dissolve readily in water or other non-organic solvents such as methanol. The formulation is a liquid and comprises of the active ingredient and additives.

Suitable liquid carriers, such as solvents, may be organic or inorganic. Water is one example of an inorganic liquid carrier. Organic liquid carriers include vegetable oils and epoxidized vegetable oils, such as rape seed oil, castor oil, coconut oil, soybean oil and epoxidized rape seed oil, epoxidized castor oil, epoxidized coconut oil, epoxidized soybean oil, and other essential oils. Other organic liquid carriers include aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Soluble powder formulations are similar to solutions in that, when mixed with water, they dissolve readily and form a true solution. Soluble powder formulations are dry and include the active ingredient and additives.

Emulsifiable concentrate formulations are liquids that contain the active ingredient, one or more solvents, and an emulsifier that allows mixing with a component in an organic liquid carrier. Formulations of this type are highly concentrated, relatively inexpensive per pound of active ingredient, and easy to handle, transport, and store. In addition, they require little agitation (will not settle out or separate) and are not abrasive to machinery or spraying equipment.

Wettable powders are dry, finely ground formulations in which the active ingredient is combined with a finely ground carrier (usually mineral clay), along with other ingredients to enhance the ability of the powder to suspend in water. Generally, the powder is mixed with water for application. Typical solid diluents are described in Watkins et al., Handbook of Insecticide Dust Diluents and Carriers, 2nd Ed., Dorland Books, Caldwell, N.J. The more absorptive diluents are preferred for wettable powders and the denser ones for dusts.

Liquid flowable formulations are made up of finely ground active ingredient suspended in a liquid. Dry flowable and water-dispersible granule formulations are much like wettable powders except that the active ingredient is formulated on a large particle (granule) instead of onto a ground powder.

The methods of making such formulations are well known. Solutions are prepared by simply mixing the ingredients. Fine, solid compositions are made by blending and, usually, grinding, as in a hammer or fluid energy mill. Suspensions are prepared by wet-milling (see, for example, U.S. Pat. No. 3,060,084).

The concentration of a pollen growth stimulating compound in a formulation may vary according to particular compositions and applications.

In some embodiments of the disclosure, inactive ingredients i.e., adjuvants) are added to pollen to improve the performance of the formulation. For example, in one embodiment of the disclosure, pollen is formulated with a surfactant. A surfactant (surface active agent) is a type of adjuvant formulated to improve the dispersing/emulsifying, absorbing, spreading, and sticking properties of a spray mixture. Surfactants can be divided into the following five groupings: (1) non-ionic surfactants, (2) crop oil concentrates, (3) nitrogen-surfactant blends, (4) esterified seed oils, and (5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical.

The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis (2-chloroethyl) ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Other adjuvants include carriers and additives, for example, wetting agents, such as anionic, cationic, nonionic, and amphoteric surfactants, buffers, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, antibiotics, fungicides, nematicides, or pesticides (others are described hereinabove). Such carriers and additives may be used in solid, liquid, gas, or gel form, depending on the embodiment and its intended application.

As used herein "artificial pollination" is the application, by hand, insects (e.g., bees) or dedicated machinery, of fertile stigmas with the pollen from plants with desired characteristics, as described herein.

Artificial pollination in the field can be achieved by pollen spraying (e.g., wet or dry spray formulations), spreading, dispersing or any other method. The application itself will be performed by ground equipment, aircraft, unmanned aerial vehicles (UAV), remote-piloted vehicles (RPV), drones or specialized robots, special vehicles or tractors, animal assisted, specialized apparatus that is designed to spread boosts of pollen, specialized apparatus that combines ventilation and spraying of pollen to enhance recycling of pollen or any other application method or apparatus wherein application can be of a single dose, multiple doses, continuous, on an hourly/daily/weekly/monthly basis or any other application timing methodology.

It will be appreciated that pollination of female flowers is necessary.

According to a specific embodiment, the whole growth area is pollinated at flowering.

According to another specific embodiment, only female flowers are pollinated while male flowers are either left untreated or treated using other means, e.g., herbicides, harvesting etc.

It will be appreciated that at any time the weed of interest can be further treated with other weed control means. For example, the weed may be treated with an herbicide (which is usually applied at early stages of germination as opposed to the pollen which is applied at flowering). Thus an herbicide for instance can be applied prior to, concomitantly with or following pollen treatment.

Any of the pollen compositions described herein can be produced as a single species pollen with a single trait for reducing weed fitness, a single species pollen with a plurality of traits for reducing weed fitness (e.g., a number of different herbicide resistances or a number of sterility encoding mechanisms) all introduced into a single weed or to a plurality of weeds of the same species, a multispecies pollen with a single trait or a multispecies pollen with a plurality of said traits.

Thus, commercial products can be manufactured as kits whereby each pollen type is packed in a separate packaging means (e.g., bag), or two or more types of pollen are combined into a single composition and packed in a single packaging means (e.g., bag). The product may be accompanied by instructions for use, regulatory information, product description and the like.

The kit may also include in a separate packaging means other active ingredients such as at least one of a chemical inducer (as described above), herbicide, fertilizer, antibiotics and the like.

Once pollen is obtained it can be used in artificial pollination of the plants under pollination conditions that inhibit growth of the plants.

As used herein "pollination conditions" refers to any one of or all of pollination timing, number of pollinations, interval between pollinations and doses used.

According to a specific embodiment, the pollination conditions refer to pollination timing.

According to such an embodiment, pollination conditions comprise pollinating at a time point not exceeding a predetermined threshold following initiation of inflorescence.

According to such an embodiment, pollination conditions comprise pollinating at a time point in which there is a predetermined threshold of initiation of inflorescence.

Methods of determining initiation of inflorescence are described in details hereinabove.

According to a specific embodiment, the pollination conditions comprise at least 20% of the plants (in the growth area) have started flowering.

According to a specific embodiment, the pollination conditions comprise at least 30% of the plants (in the growth area) have started flowering.

According to a specific embodiment, the pollination conditions comprise at least 40% of the plants (in the growth area) have started flowering.

According to a specific embodiment, the pollination conditions comprise at least 50% of the plants (in the growth area) have started flowering.

In case of dioecious plants, the plants are female plants, e.g., *A. palmeri*.

According to an additional or an alternative embodiment, the pollination conditions comprise at least 20% of the plants comprise 6-12 spikes.

According to an embodiment, pollination conditions comprise pollinating 7-30 days following time at which at least 20% of said plants exhibit stigma receptiveness and have started flowering.

According to an embodiment, pollination conditions comprise pollinating 7-21 days following time at which at least 20% of said plants exhibit stigma receptiveness and have started flowering.

According to an embodiment, pollination conditions comprise pollinating 7-14 days following time at which at least 20% of said plants exhibit stigma receptiveness and have started flowering.

According to a specific embodiment, the pollination conditions refer to number of pollinations.

According to an embodiment, the pollination is effected one.

According to a specific embodiment, the pollination is repeated in a manner that facilitates plant growth inhibition. For instance, with respect to *A. palmeri*, the present inventors were able to show that repeated administration which comprises at least a two weeks interval between pollinations exhibits a superior effect (see Example 3).

Thus, according to a specific embodiment, the pollination conditions refer to interval between pollinations.

According to a specific embodiment, the multiple pollinations are effected at intervals and wherein at least one interval of said intervals is of 3-30 days.

According to a specific embodiment, the multiple pollinations are effected at intervals and wherein at least one interval of said intervals is of 3-21 days.

According to a specific embodiment, the multiple pollinations are effected at intervals and wherein at least one interval of said intervals is of 3-14 days.

According to a specific embodiment, the multiple pollinations are effected at intervals and wherein at least one interval of said intervals is of 3-7 days.

According to a specific embodiment, the multiple pollinations are effected at intervals and wherein at least one interval of said intervals is of 7-30 days.

According to a specific embodiment, the multiple pollinations are effected at intervals and wherein at least one interval of said intervals is of 7-21 days.

According to a specific embodiment, the multiple pollinations are effected at intervals and wherein at least one interval of said intervals is of 7-14 days.

According to a specific embodiment, the multiple pollinations are effected at intervals and wherein at least one interval of said intervals is of 10-21 days.

According to a specific embodiment, the multiple pollinations are effected at intervals and wherein at least one interval of said intervals is of 14-21 days.

According to a specific embodiment, the multiple pollinations are effected at intervals and wherein at least one interval of said intervals is of 10-30 days.

According to a specific embodiment, the multiple pollinations are effected at intervals and wherein at least one interval of said intervals is of 10-45 days.

According to a specific embodiment, the multiple pollinations are effected at intervals and wherein at least one interval of said intervals is of 10-60 days.

According to a specific embodiment, the multiple pollinations are effected at intervals and wherein at least one interval of said intervals is of 14-30 days.

According to a specific embodiment, the multiple pollinations are effected at intervals and wherein at least one interval of said intervals is of 14-45 days.

According to a specific embodiment, the multiple pollinations are effected at intervals and wherein at least one interval of said intervals is of 14-60 days. According to a specific embodiment, the multiple pollinations are effected at intervals and wherein at least one interval of said intervals is of 21-45 days.

According to a specific embodiment, the multiple pollinations are effected at intervals and wherein at least one interval of said intervals is of at least 14 days.

According to a specific embodiment, the pollination conditions refer to pollen dose. It will be appreciated that the dose may increase during the duration of treatment since the plant grows as manifested by the number of inflorescences/spikes on the plant (e.g., 2-50 fold, e.g., 2-20 fold, 2-15 fold).

Table A below (which is a replica of Table 5 below) illustrates some exemplary regimen related to the Amaranth genus.

TABLE A*

| Individual/population | First treatment | Second treatment and onwards |
|---|---|---|
| Individual plant with or without chemical treatment | Total inflorescence length in cm 20-400 | Total inflorescence length is 1.3X-5X (X = last treatment) |
| Individual plant with or without chemical treatment | The plant starts to develop secondary spikes (secondary spike is at least 2 cm). | The secondary spikes are 1.3-5 times longer from last treatment |
| Population of Amaranthus plants with or without chemicals treatments | A fraction (x) of 20-50% of plants have more than 6 spikes per plant. Each spike is longer than 4 cm \ | At least 1.5X of plants have more than 6 spikes per plant compared to last treatment. Each spike is longer than 4 cm |
| Population of Amaranthus plants with or without chemicals treatments | A fraction (x) of 20-50% of plants have more than 12 spikes per plant. Each spike is longer than 4 cm | At least 1.5X of plants have more than 12 spikes per plant compared to last treatment. Each spike is longer than 4 cm |
| Population of Amaranthus plants with no chemicals treatments | A fraction (x) of 20-50% of plants have secondary spikes. the avg length of secondary spikes is longer than 2 cm (defined as X) | At least 1.5X of plants have secondary spikes compared to last treatment. the avg length of secondary spikes is longer than 2 cm |
| Population of Amaranthus plants with chemicals treatment | A fraction (x) of 20-50% of plants have more than 1 spike per plant. Each spike is longer than 4 cm (defined as X) | At least 1.5X of plants have more than 1 spike compared to last treatment. Each spike is longer than 4 cm |

*each possibility represents an independent embodiment.

According to an embodiment, the pollination conditions comprise pollinating (such as in a single pollination):
(i) when total inflorescence length per plant is 20-400 cm;
(ii) when secondary spikes initiate as manifested by a length of secondary spikes in the first pollination is at least 2 cm;
(iii) when 20-50% of the plants have more than a predetermined number of spikes per plant, each spike being longer than 4 cm;
(iv) when 20-50% of the plants have secondary spikes; and/or
(v) when 20-50% of the plants have more than 1 spike per plant longer than 4 cm.

In alternative embodiments, where multiple pollinations are used, a further pollination is performed only after a growth (e.g., an exponential growth) has been observed when compared to the previous pollination treatment. If no such growth (e.g., exponential growth) is observed no further pollination is performed since growth has reached a plateau.

According to an additional or an alternative embodiment, a first pollination of the multiple pollinations is effected when total inflorescence length per plant is 20-400 cm, an n (where n is at least 2) pollination of the multiple pollinations is effected when total inflorescence length is 1.3-5 times longer than the length at n−1 pollination of the multiple pollinations.

According to an additional or an alternative embodiment, a first pollination of the multiple pollinations is effected when secondary spikes initiate as manifested by a length of secondary spikes in the first pollination is at least 2 cm, an n pollination (where n is at least 2) of the multiple pollinations is effected when the secondary spikes are 1.3-5 times longer than in n−1 pollination of the multiple pollinations.

According to an additional or an alternative embodiment, a first pollination of the multiple pollinations is effected when a fraction of the plants have more than a predetermined number of spikes per plant, the fraction being 20-50% of the plants, each spike being longer than 4 cm, an n pollination (where n is at least 2) of the multiple pollinations is effected when at least 1.5 fold of the fraction of the plants have more than the predetermined number of spikes per plant, each spike being longer than 4 cm.

According to an embodiment, the predetermined number of spikes per plant is at least 6 (e.g., at least 7, 8, 9, 10 or 11) or at least 12.

According to an additional or an alternative embodiment, a first pollination of the multiple pollinations is effected when a fraction of the plants have secondary spikes, the fraction being 20-50% of the plants, an n pollination (where n is at least 2) of the multiple pollinations is effected when at least 1.5 fold of the fraction of the plants have the secondary spikes, a length of secondary spikes in the first pollination is at least 2 cm.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

EXAMPLES

General Procedures for Analyzing Growth Inhibition According to Some Embodiments of the Invention An effect on growth inhibition can be measured by the following parameters:
1. Percent (%) reduction in biomass at harvesting—at least 20% reduction;
2. % reduction in dry weight biomass—at least 20% reduction;
3. % reduction in number of spikes—at least 20% reduction;
4. % reduction in number of flowers—at least 20% reduction;
5. % reduction in number of inflorescences—at least 20% reduction;
6. % reduction in number of spikelets—at least 20% reduction;
7. % reduction in number of flowers in the spikelets—at least 20% reduction;

Effect of timing can be determined by the following parameters:
1. Interval—every 3D, every 1 week, every 10 days, every 2 weeks, every 2.5 weeks, every 3 weeks, every 4 weeks, every 5 weeks, every 2 months.
2. Time of first application—
2.1 In terms of measuring flowering initiation over the entire field, the following time of applications are used:

One week after initiation of flowering, 10 days after initiation of flowering, two weeks, after about 20% of weeds in a field have initiated flowering, after about 50% of weeds in a field have initiated flowering, after about 20% of weeds in the field have initiated to develop secondary spikes, after about 50% of weeds in the field have initiated to develop secondary spikes, when the average number of flower heads of all plants reaches 1.5-4, when the average number of inflorescence with receptive stigma in all plants reaches 1.5-4, when the average number of inflorescence with receptive stigma in all plants reaches 4-8, when the average number of inflorescence with receptive stigma in all plants reaches 6-10, when the average percent of leaf axils that developed flowers reaches at least 20% (of total leaf axils in the life cycle), when the average percent of leaf axils that contain inflorescence reaches at least 50%.

2.2 Status of plants that the treatments is applied onto—
    $1^{st}$ application:
Number of flowering spikes is at least 6 spikes;
Number of flowering spikes is at least 8 spikes;
Number of flowering spikes is at least 10 spikes;
Number of flowering spikes is at least 12 spikes
Number of flowering spikes is at least 14 spikes;
Number of flowering spikes is at least 16 spikes;
Number of flowering spikes is at least 18 spikes; or
Number of flowering spikes is at least 20 spikes.
The weed plant starts developing secondary spikes.
Number of flower heads is at least 2.
Number of flower heads is at least 4.
Number of flower heads is at least 6.
Number of flower heads is at least 8.
Number of flower heads is at least 10.
Number of inflorescences with receptive stigma is at least 2.
Number of inflorescences with receptive stigma is at least 4.
Number of inflorescences with receptive stigma is at least 6.
Number of inflorescences with receptive stigma is at least 8.
Number of inflorescences with receptive stigma is at least 10.
Percent of leaf axils that contain inflorescence reaches at least 20%.
Percent of leaf axils that contain inflorescence reaches at least 50%

Status of plants that the treatments is applied onto—$1^{st}$ application following chemical application:
Number of flowering spikes is at least 1 spike;
Number of flowering spikes is at least 2 spikes;
Number of flowering spikes is at least 4 spikes;
Number of flowering spikes is at least 6 spikes;
Number of flowering spikes is at least 8 spikes;
Number of flowering spikes is at least 10 spikes;
Number of flowering spikes is at least 12 spikes
Number of flowering spikes is at least 14 spikes;
Number of flowering spikes is at least 16 spikes;
Number of flowering spikes is at least 18 spikes; or
Number of flowering spikes is at least 20 spikes.
The weed plant starts to develop secondary spikes.
Number of flower heads is at least 1.
Number of flower heads is at least 2.
Number of flower heads is at least 4.
Number of flower heads is at least 6.
Number of flower heads is at least 8.
Number of flower heads is at least 10.

Number of inflorescences with receptive stigma is at least 1.
Number of inflorescences with receptive stigma is at least 2.
Number of inflorescences with receptive stigma is at least 4.
Number of inflorescences with receptive stigma is at least 6.
Number of inflorescences with receptive stigma is at least 8.
Number of inflorescences with receptive stigma is at least 10.
Percent of leaf axils that contain inflorescence reaches at least 2.0%,
Percent of leaf axils that contain inflorescence reaches at least 50%

In the case of *Amaranthus* weeds, flowering is determined when spikes are at least in the length of 3 cm or 5 cm.

Example 1: Inhibition of Plant Development Following Artificial Pollination with X-Ray Irradiated Pollen in *A. palmeri*

Sixteen female *A. palmeri* plants germinated in a Conviron growth chamber under conditions of 34° C./24° C. 16/8 day/night. When plant height reached approximately 30 cm they were transferred to the greenhouse and continued their growth (with natural daylength in Israel during January and temperature ranging from a minimum of 16° C. to a maximum of 40° C.). One day before the experiment started the female plants were transferred into growth rooms in which the conditions were 34° C./24° C. with a photoperiod of 16/8 h day/night.

The 16 female plants were divided into two groups in the following manner: the 16 female plants were divided to pairs that are similar in their developmental stage and have a similar size. One female of each pair was assigned to the control group while the other female was assigned to the treatment group.

During morning hours *A. palmeri* pollen was collected for two consecutive days from male plants that were grown in a greenhouse (with natural daylength in Israel during January and temperature ranging from a minimum of 16° C. and a maximum of 40° C.). Pollen was X-ray irradiated with a dose of 150 Gy.

One group of 8 female plants was taken out from the growth room for artificial pollination. The artificial pollination was conducted with a hand sprayer with 1.3 gr of the irradiated pollen plus 0.65 gr of Talc so on average each female plant was pollinated with 162.5 mg of pollen. After 2 hours the 8 female plants were returned to the growth room and continued to grow with the non-treated (non-pollinated) group. Several morphological parameters were measured at the beginning of the experiment, i.e., on day 14 and 24 days from the pollination event (day 0). A clear trend of reduction in the total number of spikes was observed (see Table 1 below).

TABLE 1

| | Average number of spikes per plant | | | SE | | |
|---|---|---|---|---|---|---|
| | 0 DAT | 14 DAT | 24 DAT | 0 DAT | 14 DAT | 24 DAT |
| Control (Not-pollinated) | 31.625 | 58.375 | 69.625 | 5.9 | 12.69 | 15.3 |

TABLE 1-continued

| | Average number of spikes per plant | | | SE | | |
|---|---|---|---|---|---|---|
| | 0 DAT | 14 DAT | 24 DAT | 0 DAT | 14 DAT | 24 DAT |
| Single Pollination treatment | 33.5 | 47.75 | 53.5 | 7.49 | 9.5 | 10.6 |

DAT = Days after treatment

At the end of the experiment (24 days after the pollination event) the control group had on average 38 additional spikes versus only 20 in the treated group. Thus overall there was an average reduction of 47% in the number of new spikes with a p-value of 0.08.

TABLE 2

| | Difference in number of new spikes between 0 DAT and 24 DAT | | |
|---|---|---|---|
| | Average | SE | Paired t-test |
| Not-pollinated | 38 | 13.76 | 0.08 |
| Single Pollination | 20 | 6.23 | |

Example 2: Inhibition of Plant Development Following Artificial Pollination with X-Ray Irradiated Pollen in *A. palmeri* in Intervals of 1 Week Twenty female plants that were grown in a net-house were divided into two groups in the following manner: They were divided to pairs that are similar in their developmental stage and have similar size. One female of each pair was assigned to one group while the other female was assigned to the other group.

Pollen was collected from *A. palmeri* male plants that were grown in a net house during morning hours for several days. The pollen was X-ray irradiated with a dose of 300Gy and stored for two weeks at 9° C.

One group of female *A. palmeri* plants received treatment of artificial pollination with the X-ray irradiated pollen 3 times with intervals of 1 week between treatments, such that the plants were treated on day 1, 8 and 15 from experiment start day (morphological parameters were taken on day 0), while the other group was not pollinated at all.

Various morphological parameters including plant height, main spike length, $5^{th}$ spike length (from the top), number of primary spikes and number of secondary spikes were measured and recorded for all the 20 plants in 3 time points during the experiment at day 0, 12 and 27 from experiment start day.

Clear reduction in the average number of secondary spikes was found between the group that was artificially pollinated with the X-ray irradiated pollen versus the group that did not receive the treatment (see Table 3 below).

TABLE 3

| 26 days after first pollination | No-treatment | Treated |
|---|---|---|
| Average number of secondary spikes per femalelant | 93.5 | 65.4 |

TABLE 3-continued

| 26 days after first pollination | No-treatment | Treated |
|---|---|---|
| SD | 58.37 | 31.05 |
| P-value of T-test | | 0.098 |
| Percent reduction | | 30% |

Example 3: Inhibition of Plant Growth and Development Following Artificial Pollination with X-Ray Irradiated Pollen in *A. palmeri* Under Field Conditions The experiment was conducted in Rehovot region during summer of 2018. The experiment included 16 plots, each of size 5×5 m, with 4 m of inter-plot borders of dense corn that their role was to minimize pollen contamination between the plots. Corn was sown at the border regions in high density of 10-12 plants/meter and two weeks after corn was sown inside the plots in density of 6-8 plants/meter. Eight days after *A. plameri* seeds were sown inside the plots to achieve final density of 1 plant every 90 cm (4 seeds were sown in each hole and were thinned after germination).

The experiment included 4 treatment regimens: 1) No-treatment control; 2) Application of X-ray irradiated pollen every 3-days (3D); 3) Application of X-ray irradiated pollen every week; and 4) Application of X-ray irradiated pollen every two weeks. Each treatment was applied in 4 plots that were randomly distributed between all the 16 plots.

On June 14$^{th}$ the first pollen treatment was applied in the every 3-days regimen plots. On June 21$^{st}$ the first pollen treatment was applied in the every-week regimen plots. And on June 26$^{th}$ the first pollen treatment was applied in the every-two weeks regimen plots. No additional pollen was applied in the control plots—these plots were only pollinated by natural pollination.

The treated pollen that was used for all applications was collected from *A. palmeri* male plants that were grown in a separate net-house and was collected during morning hours for several consecutive days (according to the pollen needed amount). Pollen was X-ray irradiated with a dose of 300Gy.

The artificial pollination was conducted using a pollen mini-duster machine (kiwi pollen mini-duster www(dot)kiwipollen(dot)com/dry-applicators/). Pollen was mixed with Talc in ratio of 1:1 or 2:1 in order to reduce amounts of pollen used per artificial pollination. Pollination procedure was conducted in a way that all *A. palmeri* female inflorescences were sprayed with the treated pollen mixture. As during the flowering season *A. palmeri* plants size, the number of inflorescences and their size increased, the amount of pollen that was used to cover all the inflorescences increased respectively. Therefore, the average amount of pollen used per plot per treatment was not constant and ranged from 0.625 g to 10 g per the above mentioned-density.

On August 16$^{th}$, last pollen treatment was applied to all the treated plots. After 2 hours all *A. palmeri* male plants were harvested and *A. plameri* female plants continued growing for additional 16 days in order to allow all the seeds to reach full maturity.

On September 2-4 the experiment was harvested, namely all the above-ground material of each *A. palmeri* female plant was cut and was placed in large bags. Two hours after harvesting *A. palmeri* female plants were weighed and were placed in the bag for drying in controlled growing rooms with 34° C./24° C. day/night conditions for at least 1 month. After the drying procedure, plants were weighed again (Dry weight measurement). In addition, the total number of spikes on each female plant was counted. Statistical analysis was conducted for all these measures in all the examined treatment regimens. The average and standard deviation were calculated for each treatment. T-test statistics for each measure were calculated when comparing the no-treatment control with each of the examined treatment regimens (see Table 4 below).

TABLE 4

| | No-treatment control | Every 3 days treatment | Every week treatment | Every two weeks treatment |
|---|---|---|---|---|
| | | Weight at harvest | | |
| Average (g) | 566.9565 | 352.6 | 418.6667 | 227.1452 |
| SE (g) | 102.7105 | 37.81241 | 57.90957 | 31.2929 |
| P-value of T-test | | 0.038151 | 0.182337 | 0.000494 |
| | | Dry weight | | |
| Average (g) | 220.3478 | 132.5 | 179.1525 | 100.3548 |
| SE (g) | 35.50698 | 13.29543 | 23.96873 | 14.11753 |
| P-value of T-test | | 0.016101 | 0.317919 | 0.000687 |
| | | Number of Spikes | | |
| Average | 159 | 106.9038 | 149.15 | 79.59016 |
| SE | 23.56907 | 12.52747 | 20.4408 | 11.53435 |
| P-value of T-test | | 0.044434 | 0.75025 | 0.001399 |

Example 4: Inhibition of Plant Growth and Development Following Artificial Pollination with X-Ray Irradiated Pollen in *Alopecurus myosuroides* Under Net-House Conditions Twelve Black grass (*Alopecurus myosuroides*) seeds are germinated inside a net house at the beginning of January.

The seedlings are moved to pots and continue to grow in the net house under natural daylength and temperature during the winter times in Israel.

Four weeks after germination, each plant is split to two so as to obtain 2 plants which are genetically identical (the plants are split before the transition from vegetative stage to reproductive stage). Each such "clone" is sown in a pot while one of them is classified as the control treatment while the other is classified as the treatment group. Both groups continue to grow under the same conditions and all plants are being tracked on a daily basis to identify flower heads. The pots of each group are arranged in such a way that allow natural cross pollination between them (but not between the control and treatment groups). When the average number of flower heads of all plants reaches 2.5, artificial pollination of plants that belong to the treatment group is conducted with X-Ray irradiated pollen (e.g., as disclosed in PCT Publication No. WO2019/106666) with the necessary modifications). The pollination procedure is conducted by spraying each plant with 80 mg of treated pollen diluted in 80 mg of talc using a small scale puffer. Six weeks after the first flower head appears, the experiment is ended and for each plant the total number of flower heads is being recorded. In addition, all plants are cut and placed in bags for drying and the dry weight of each plant is recorded. The average and standard deviation (SD) of these parameters is calculated, and statistical analysis is conducted in order to evaluate the decrease in these parameters due to the pollination treatment.

Example 5: Inhibition of Plant Growth and Development Following Multiple Artificial Pollinations with X-Ray Irradiated Pollen in *Alopecurus myosuroides* Under Net-House Conditions Twelve Black grass (*Alopecurus myosuroides*) seeds are germinated inside a net house on the beginning of January. The seedlings are moved to pots and continue to grow in the net house under natural daylength and temperature during the winter times in Israel.

Four weeks after germination, each plant is split to two so as to obtain 2 plants which are genetically identical (the plants are split before the transition from vegetative stage to reproductive stage). Each such "clone" is sown in a pot. One week after the plants are split, the plants are divided (before flowering) into 6 treatment groups in such a way that each group includes one "clone" from each plant. The following are the 6 different treatment groups:

1. Control I—All 12 plants grow together one next to the other to allow natural cross pollination.
2. Blank control—Each plant grows in a cage to avoid pollination (these plants will have no seeds).
3. Treatment A—All plants grow together similar to 'Control I' and when the average flower heads of all plants reaches 2.5 they are artificially pollinated with X-Ray irradiated pollen (e.g., as disclosed in PCT Publication No. WO2019/106666 with the necessary modifications).
4. Treatment B—Each plant grows in a cage similar to the 'Blank control' treatment and when the average flower heads per plant reaches 2.5, they are artificially pollinated with X-Ray irradiated pollen (e.g., as disclosed in PCT Publication No. WO2019/106666 with the necessary modifications).
5. Treatment C—All plants grow together similar to 'Control I' and when the average flower heads of all plants reaches 2.5 they are artificially pollinated with X-Ray irradiated pollen. When the average flower heads of all plants reaches 5, additional artificial pollination treatment with X-Ray irradiated pollen is conducted.
6. Treatment D—Each plant grows in a cage similar to 'Blank control' and when the average flower heads of all plants reaches 2.5 they are artificially pollinated with X-Ray irradiated pollen. When the average flower heads of all plants reaches 5, additional artificial pollination treatment with X-Ray irradiated pollen is conducted.

The 6 groups are grown in the same net house, but are separated into 4 using PVC and each treatment is in a different side of the net house (the 3 treatments in which the plants are in a cage grow together.)

Each pollination procedure is conducted by spraying each plant with 80 mg of treated pollen diluted in 80 mg of talc using small scale puffer.

Six weeks after the first flower head appears the experiment is ended and the total number of flower heads per plant is being recorded. In addition, all plants are cut and placed in bags for drying and the dry weight of each plant is recorded. The average and SD of these parameters are calculated, and statistical analysis is conducted in order to evaluate the decrease in these parameters in the various treatments.

Example 6: Inhibition of Plant Growth and Development Following Artificial Pollination with X-Ray Irradiated Pollen *Lolium* sp. (*Lolium multiflorum, Lolium Rigidum, Lolium Perenne*) Under Net-House Conditions The experiment is conducted with *L. perenne* or *L. rigidum* or *L. multiflorum* similarly to Example 4 only with the following differences:

The treatment is applied when the average number of inflorescences with receptive stigma in all plants reaches 2.5.

The examined parameters that are evaluated at the end of the experiment in order to demonstrate the growth inhibition are: number of Inflorescence per plant, number of Spikelet per Inflorescence and number of flowers per spikelet as well as dry weight of each plant.

Example 7: Inhibition of Plant Growth and Development Following Multiple Artificial Pollination with X-Ray Irradiated Pollen *Lolium* sp. (*Lolium multiflorum, Lolium Rigidum, Lolium Perenne*) Under Net-House Conditions The experiment is conducted with *L. perenne* or *L. rigidum* or *L. multiflorum* similarly to Example 5 only with the following differences:

The treatment is applied when the average number of inflorescences with receptive stigma in all plants reaches 2.5.

The examined parameters that are evaluated at the end of the experiment in order to demonstrate the growth inhibition are: number of Inflorescence per plant, number of Spikelet per Inflorescence and number of flowers per spikelet as well as dry weight of each plant.

Example 8: Inhibition of Plant Development Following Artificial Pollination with X-Ray Irradiated Pollen in *Kochia* (*Kochia scoperia=Bassia scoperia*)

Sixteen *Kochia scoperia* plants are germinated in a Conviron growth chamber under conditions of 34 C/24 C 16/8 day/night. When plant height reaches approximately 10 cm they are transferred to a net house to continue their growth under natural daylength and temperature during the summer times in Israel.

The 16 plants are divided into two groups in the following manner: the 16 plants are divided to pairs that are similar in their developmental stage and have similar size, One plant of each pair is assigned to the control group while the other plant is assigned to the treatment group (X-ray irradiated pollen is produced as disclosed in PCT Publication No. WO2019/106666 with the necessary modifications).

When the average percent of leaf axils that contain inflorescence reaches at least 20%, a group of 8 plants is taken out from the net house for artificial pollination. The pollination procedure is conducted by spraying each plant with 80 mg of treated pollen diluted in 120 mg of talc using a small scale puffer. After 2 hours, the 8 plants are returned to the net house and continue to grow with the non-treated (non-pollinated) group. Several morphological parameters are measured at the beginning of the experiment such as plant height, number of spikes and number of inflorescences. 45 days from the pollination event the experiment is ended and for each plant the percent leaf axils that contain inflorescence is estimated and recorded. In addition, all plants are cut and placed in bags for drying and the dry weight of each plant is recorded. The average and SD of these parameters are calculated, and statistical analysis is conducted in order to evaluate the decrease in these parameters due to the pollination treatment.

Example 9: Inhibition of Plant Development Following Artificial Pollination with X-Ray Irradiated Pollen in Kochia (Kochia scoperia=Bassia scoperia) in a Few Intervals Twenty-four Kochia scoperia plants are germinated in a Conviron growth chamber under conditions of 34 C/24 C 16/8 day/night. When plant height reaches approximately 10 cm they are transferred to a net house to continue their growth under natural daylength and temperature during the summer times in Israel.

The 24 plants are divided into three groups of 8 plants each, such that each group includes plants that are similar in the distribution of their developmental stage and have similar distribution of plant size. The groups are: control, treatment A and treatment B (X-ray irradiated pollen is produced as disclosed in PCT Publication No. WO2019/106666 with the necessary modifications).

When the average percent of leaf axils that contain inflorescence reaches at least 20% the plants from treatment A and treatment B are taken out from the Net house for artificial pollination. Treatment A plants are artificially pollinated every week for 3 weeks. Treatment 13 plants are artificially pollinated again when the average percent of leaf axils that contain inflorescence reaches 40% and 60%. After 2 hours the plants are returned to the net house and continue to grow with the non-treated (non-pollinated) group. Several morphological parameters are measured at the beginning of experiment such as plant height and number of inflorescences. 45 days from the first pollination event, the experiment is ended and for each plant the percent of joint regions of shoot and leaf that contain inflorescence is estimated and recorded. In addition, all plants are cut and placed in bags for drying and the dry weight of each plant is recorded. The average and SD of these parameters are calculated, and a statistical analysis is conducted in order to evaluate the decrease in these parameters due to the pollination treatments.

Example 10: Inhibition of Plant Development Following Artificial Pollination with X-Ray Irradiated Pollen in Ambrosia sp. (Ambrosia artemisiifolia, Ambrosia trifida, Ambrosia confertiflora)

Sixteen A. artemisiifolia plants are germinated in a Conviron growth chamber under conditions of 34 C/24 C 16/8 day/night. When plant height reaches approximately 30 cm they are transferred to a net house to continue their growth under natural daylength and temperature during the summer times in Israel.

The 16 plants are divided into two groups in the following manner: the 16 plants are divided to pairs that are similar in their developmental stage and have similar size, One plant of each pair is assigned to the control group while the other plant is assigned to the treatment group (X-ray irradiated pollen is produced as disclosed in PCT Publication No. WO2019/106666 with the necessary modifications).

When the average number of inflorescences of all plants reaches 6, a group of 8 plants is taken out from the net house for artificial pollination. The artificial pollination is conducted with a hand sprayer with 100 mg of the irradiated pollen plus 200 mg of Talc per treated plant. After 2 hours the 8 plants are returned to the net house and continue to grow with the non-treated (non-pollinated) group. Several morphological parameters are measured at the beginning of the experiment such as plant height and number of inflorescences. 30 days from the pollination event, the experiment is ended. For each plant the total number of inflorescences is being recorded as well as the plant height and the inflorescences length. In addition, all plants are cut and placed in bags for drying and the dry weight of each plant is recorded. The average and SD of these parameters are calculated, and statistical analysis is conducted in order to evaluate the decrease in these parameters due to the pollination treatment.

Similar experiments are conducted with A, trifida and A. confertiflora weeds and a similar statistical analysis is conducted in order to evaluate the level of growth inhibition following the treatment in these weeds.

Example 11: Inhibition of Plant Development Following Artificial Pollination with X-Ray Irradiated Pollen in Ambrosia sp (Ambrosia artemisiifolia, Ambrosia trifida, Ambrosia confertiflora) in Few Intervals Twenty-four A. artemisiifolia plants are germinated in a Conviron growth chamber under conditions of 34 C/24 C 16/8 day/night. When the plants height reach approximately 30 cm they are transferred to a net house to continue their growth under natural daylength and temperature during the summer times in Israel.

The 24 plants are divided into three groups of 8 plants each so each group includes plants that are similar in the distribution of their developmental stage and have similar distribution of plant size. The groups are: control, treatment A and treatment B (X-ray irradiated pollen is produced as disclosed in PCT Publication No. WO2019/106666 with the necessary modifications).

When the average number of inflorescences of all plants reaches 6, the plants from treatment A and treatment B are taken out from the net house for artificial pollination. Treatment A plants continue to be artificially pollinated every week for 3 weeks. Treatment B plants continue to be artificially pollinated when the average number of inflorescences of all plants in the group reaches 12 and 18. Each artificial pollination procedure is conducted with a hand sprayer with 100 mg of the irradiated pollen plus 200 mg of Talc per treated plant. After 2 hours the plants are returned to the net house and continue to grow with the non-treated (non-pollinated) group.

Several morphological parameters are measured at the beginning of the experiment such as plant height and the number of inflorescences. 30 days following the first pollination event, the experiment is ended. For each plant the total number of inflorescences is being recorded as well as plant height and inflorescences length. In addition, all plants are cut and placed in bags for drying and the dry weight of each plant is recorded. The average and SD of these parameters are calculated, and a statistical analysis is conducted in order to evaluate the decrease in these parameters due to the pollination treatments.

Similar experiments are conducted with *A. trifida* and *A. confertiflora* weeds and similar statistical analysis is conducted in order to evaluate the level of growth inhibition that obtained following the treatment in these weeds.

Example 12: Inhibition of Plant Development Following Artificial Pollination with X-Ray Irradiated Pollen in *Chenopodium album*

The experiment is conducted with *Chenopodium album* similarly to Example 10.

Example 13: Inhibition of Plant Development Following Artificial Pollination with X-Ray Irradiated Pollen in *Chenopodium album* in Few Intervals The experiment is conducted with *Chenopodium album* similarly to Example 11.

Example 14: Inhibition of Plant Development Following Artificial Pollination with X-Ray Irradiated Pollen in *Apera spica-Venti*

The experiment is conducted similarly to Example 4 only with *Apera spica-venti* weed species.

Example 15: Inhibition of Plant Development Following Artificial Pollination with X-Ray Irradiated Pollen in *Apera spica-venti* in Few Intervals The experiment is conducted similarly to Example 5 only with *Apera spica-venti* weed species.

Example 16: Treatment Regimen for Reducing Growth in *A. palmeri*

TABLE 5

| Individual/population | First treatment | Second treatment and onwards |
|---|---|---|
| Individual plant with or without chemical treatment | Total inflorescence length in cm 20-400 | Total inflorescence length is 1.3X-5X (X = last treatment) |
| Individual plant with or without chemical treatment | The plant starts to develop secondary spikes (secondary spike is at least 2 cm). | The secondary spikes are 1.3-5 times longer from last treatment |
| Population of Amaranthus plants with or without chemicals treatments | A fraction (x) of 20-50% of plants have more than 6 spikes per plant. Each spike is longer than 4 cm \ | At least 1.5X of plants have more than 6 spikes per plant compared to last treatment. Each spike is longer than 4 cm |
| Population of Amaranthus plants with or without chemicals treatments | A fraction (x) of 20-50% of plants have more than 12 spikes per plant. Each spike is longer than 4 cm | At least 1.5X of plants have more than 12 spikes per plant compared to last treatment. Each spike is longer than 4 cm |
| Population of Amaranthus plants with no chemicals treatments | A fraction (x) of 20-50% of plants have secondary spikes. the avg length of secondary spikes is longer than 2 cm (defined as X) | At least 1.5X of plants have secondary spikes compared to last treatment. the avg length of secondary spikes is longer than 2 cm |
| Population of Amaranthus plants with chemicals treatment | A fraction (x) of 20-50% plants have more than 1 spike per plant. Each spike is longer than 4 cm (defined as X) | At least 1.5X of of plants have more than 1 spike compared to last treatment. Each spike is longer than 4 cm |

In addition, any priority document(s) of this application is/are hereby incorporated herein by reference in its/their entirety.

What is claimed is:

1. A method of inhibiting growth of a plurality of plants of a weed species of interest being *Amaranthus palmeri* or *Alopecurus myosuroides* in a growth area, the method comprising, artificially pollinating inflorescences of said plants with irradiated pollen that reduces fitness of said plants, said artificially pollinating is performed under pollination conditions that inhibit growth of the plants wherein said conditions comprise:
   (i) at least 20% of the plants in the growth area are flowering female plants having more than 1 spike per plant longer than 4 cm; and
   (ii) competition with native pollination,
   wherein said inhibiting growth is manifested by a reduced vegetative biomass of the plurality of plants as compared to control plants of said weed species of interest not treated with said pollen, being in the same growth conditions and harvesting time from germination.

2. The method of claim 1, wherein said biomass is dry weight.

3. The method of claim 1, wherein said inhibiting growth is further manifested by at least one of:

a reduced number of inflorescences in a life-cycle of the plants as compared to control plants of said weed species of interest not treated with said pollen, being in the same growth conditions and harvesting time from germination;

a reduced number of spikes in a life-cycle of the plants as compared to control plants of said weed species of interest not treated with said pollen, being of in the same growth conditions and harvesting time from germination;

a reduced number of secondary spikes in a life-cycle of the plants as compared to control plants of said weed species of interest not treated with said pollen, being in the same growth conditions and harvesting time from germination;

a reduced number of spikelets per inflorescence in a life-cycle of the plants as compared to control plants of said weed species of interest not treated with said pollen, being in the same growth conditions and harvesting time from germination;

a reduced number of flowers per spikelets in a life-cycle of the plants as compared to control plants of said weed species of interest not treated with said pollen, being in the same growth conditions and harvesting time from germination;

a reduced number of flowers in a life-cycle of the plants as compared to control plants of said weed species of interest not treated with said pollen, being in the same growth conditions and harvesting time from germination;

a reduced fraction of leaf axils that developed flowers in a life-cycle of the plants as compared to control plants of the weed species of interest not treated with the pollen, being in the same growth conditions and harvesting time from germination.

4. The method of claim 1, wherein said pollination conditions comprise a single pollination or multiple pollinations.

5. The method of claim 4, wherein said multiple pollinations are effected at intervals and wherein at least one interval of said intervals is of 10-21 days.

6. The method of claim 1, wherein said inhibition of growth is by at least 20% as compared to control plants of said weed species of interest not treated with said pollen, being in the same growth conditions and harvesting time from germination.

7. The method of claim 1, wherein said irradiated pollen is achieved with x-ray or gamma ray.

8. The method of claim 1, wherein said at least 20% of the plants in the growth area are flowering female plants is at least 50%.

9. The method of claim 1, wherein said pollination conditions comprise at least 20% of the plants comprise 6-12 spikes.

10. The method of claim 1, said pollination conditions comprise pollinating 7-30 days following time at which at least 20% of said plants exhibit stigma receptiveness and have started flowering.

11. The method of claim 1, wherein said pollination conditions comprise pollinating:
(i) when total inflorescence length per plant is 20-400 cm;
(ii) when secondary spikes initiate as manifested by a length of secondary spikes in said first pollination is at least 2 cm;
(iii) when 20-50% of the plants have more than a predetermined number of spikes per plant, each spike being longer than 4 cm;
(iv) when 20-50% of the plants have secondary spikes; and/or
(v) when 20-50% of the plants have more than 1 spike per plant longer than 4 cm.

12. The method of claim 4, wherein a first pollination of said multiple pollinations is effected when:
total inflorescence length per plant is 20-400 cm, an n (where n is at least 2) pollination of said multiple pollinations is effected when total inflorescence length is 1.3-5 times longer than said length at n−1 pollination of said multiple pollinations;
secondary spikes initiate as manifested by a length of secondary spikes in said first pollination is at least 2 cm, an n pollination (where n is at least 2) of said multiple pollinations is effected when said secondary spikes are 1.3-5 times longer than in n−1 pollination of said multiple pollinations; or
a fraction of the plants have more than a predetermined number of spikes per plant, said fraction being 20-50% of the plants, each spike being longer than 4 cm, an n pollination (where n is at least 2) of said multiple pollinations is effected when at least 1.5 fold of said fraction of the plants have more than said predetermined number of spikes per plant, each spike being longer than 4 cm.

13. The method of claim 11, wherein said predetermined number of spikes per plant is at least 6 or at least 12.

14. The method of claim 4, wherein a first pollination of said multiple pollinations is effected when a fraction of the plants have secondary spikes, said fraction being 20-50% of the plants, an n pollination (where n is at least 2) of said multiple pollinations is effected when at least 1.5 fold of the fraction of the plants have said secondary spikes, a length of secondary spikes in said first pollination is at least 2 cm.

15. The method of claim 4, wherein a first pollination of said multiple pollinations is effected when a fraction of the plants have more than 1 spike per plant longer than 4 cm, said fraction being 20-50% of the plants, an n pollination (where n is at least 2) of said multiple pollinations is effected when at least 1.5 fold of the fraction of the plants have more than 1 spike per plant longer than 4 cm.

16. The method of claim 1, wherein said weed species of interest is an herbicide resistant weed.

17. The method of claim 1, further comprising treating said plants with an herbicide.

18. The method of claim 17, wherein said treating is prior to said pollinating.

* * * * *